(12) United States Patent
Hayashi et al.

(10) Patent No.: US 9,818,654 B2
(45) Date of Patent: Nov. 14, 2017

(54) SUBSTRATE PROCESSING APPARATUS AND SUBSTRATE PROCESSING METHOD

(71) Applicant: Tokyo Electron Limited, Tokyo (JP)

(72) Inventors: Masato Hayashi, Koshi (JP); Kohei Noguchi, Koshi (JP); Kenji Iizuka, Koshi (JP); Naruaki Iida, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 0 days.

(21) Appl. No.: 15/171,240

(22) Filed: Jun. 2, 2016

(65) Prior Publication Data

US 2016/0358829 A1    Dec. 8, 2016

(30) Foreign Application Priority Data

Jun. 3, 2015  (JP) ................................. 2015-113240

(51) Int. Cl.
*H01L 21/027*   (2006.01)
*H01L 21/66*    (2006.01)
(Continued)

(52) U.S. Cl.
CPC ............. *H01L 22/10* (2013.01); *G01N 21/85* (2013.01); *G03F 7/16* (2013.01);
(Continued)

(58) Field of Classification Search
CPC ................. H01L 22/10; H01L 21/0273; H01L 21/67253; G01N 21/85
See application file for complete search history.

(56) References Cited

U.S. PATENT DOCUMENTS 4,861,137 A *  8/1989  Nagata ................... G02B 7/022
                                                     257/E33.067
7,965,386 B2 *  6/2011  Urano ................ G01N 21/9501
                                                         356/237.2
(Continued)

FOREIGN PATENT DOCUMENTS

JP    2004-327638 A    11/2004
JP    2011-181766 A     9/2011

*Primary Examiner* — Kyoung Lee
*Assistant Examiner* — Christina Sylvia
(74) *Attorney, Agent, or Firm* — Burr & Brown, PLLC

(57) ABSTRACT

An apparatus includes: measurement flow passage portions as part of a respective plurality of supply paths of fluids to be supplied to a substrate, the measurement flow passage portions constituting measurement regions for measurement of foreign matter in the fluids, and being disposed so as to form a row with each other; a light irradiating unit configured to form an optical path in one of the flow passage portions, the light irradiating unit being shared by the plurality of flow passage portions; a moving mechanism configured to move the light irradiating unit relatively along a direction of arrangement of the flow passage portions to form the optical path within the flow passage portion selected among the plurality of flow passage portions; a light receiving unit including a light receiving element, the light receiving element receiving light transmitted by the flow passage portion; and a detecting unit configured to detect foreign matter in the fluid on a basis of a signal output from the light receiving element. Consequently, the number of necessary light irradiating units can be reduced, and the apparatus can be miniaturized.

12 Claims, 12 Drawing Sheets

(51) Int. Cl.
*H01L 21/67* (2006.01)
*G01N 21/85* (2006.01)
*G03F 7/16* (2006.01)

(52) U.S. Cl.
CPC ............ *H01L 21/67253* (2013.01); *G01N 2021/8578* (2013.01); *H01L 21/0273* (2013.01)

(56) References Cited

U.S. PATENT DOCUMENTS

| | | | | |
|---|---|---|---|---|
| 2006/0147350 A1* | 7/2006 | Sugita | ............... | G01N 21/41 422/400 |
| 2009/0187354 A1* | 7/2009 | Ooyama | ............ | G01B 11/306 702/40 |
| 2012/0004864 A1* | 1/2012 | Tsukii | ................ | G01F 1/7086 702/49 |

* cited by examiner

SUBSTRATE PROCESSING APPARATUS AND SUBSTRATE PROCESSING METHOD

CROSS-REFERENCE TO RELATED APPLICATIONS

This application is based upon and claims the benefit of priority from Japanese Patent Application No. 2015-113240, filed on Jun. 3, 2015; the entire contents of which are incorporated herein by reference.

BACKGROUND OF THE INVENTION

Field of the Invention

The present invention relates to a substrate processing apparatus and a substrate processing method for processing a substrate by supplying a fluid to the substrate.

Background Art

In a photolithography process in a semiconductor device manufacturing process, a semiconductor wafer (hereinafter described as a wafer) is supplied with various kinds of chemicals such as resists and the like to process the wafer. A chemical supply device that thus supplies a chemical to process the wafer includes for example a supply source of the chemical, a nozzle discharging the chemical to the wafer, and a supply path connecting the nozzle and the supply source to each other.

Minute foreign matter, such as particles, air bubbles, or the like, may be mixed in the chemical flowing through the above-described supply path. When air bubbles are mixed in a chemical for forming a film on the wafer, such as a resist or the like, the film formed on the wafer may be chipped. When particles are mixed, the particles may function as an unintended mask in an etching process after the photolithography process. When such an abnormality in the film formation and such an abnormality in the etching occur, the yield of the semiconductor device is decreased. Thus, detection of the foreign matter included in the chemical in the above-described supply path has been studied. Japanese Patent Application No. 2004-327638, for example, describes providing a detecting mechanism including an irradiating unit applying laser light and a light receiving unit in a supply path of a chemical supply device, and optically detecting the number of air bubbles in a chemical running through the supply path. In addition, Japanese Patent Application No. 2011-181766 describes a technology in which a sensor for detecting a strain is provided to a supply path and a nozzle of a chemical supply device to detect air bubbles.

A plurality of chemical supply paths may be provided to one chemical supply device. For example, as a chemical supply device, there is a resist coating device that coats a wafer with a resist as a chemical to form a resist film. This device may be provided with a plurality of resist supply paths in order to be able to coat the wafer with one resist selected from a plurality of kinds of resists. Further, the resist coating device may also be provided with a supply path supplying the wafer with a chemical for increasing wettability of the surface of the wafer, as will be described in an embodiment of the invention.

In the device thus including many chemical supply paths, the optical detecting mechanism described in Japanese Patent Application No. 2004-327638 may be provided for each supply path. However, in the case where the detecting mechanism is thus provided for each supply path, because an optical system constituting the detecting mechanism generally has a relatively large size, the chemical supply device is increased in size, and also the manufacturing cost of the device is increased. Japanese Patent Application No. 2011-181766 does not disclose any measure to prevent an increase in size of the chemical supply device and an increase in the manufacturing cost in a case where the chemical supply device has a plurality of supply paths.

The description has been made of problems when foreign matter is mixed in a chemical. However, in various kinds of devices used in the photolithography process, such as the above-described chemical supply device and the like, a gas is supplied to a wafer processing atmosphere. An abnormality may occur also in a case where foreign matter is mixed in the gas, as in the case where foreign matter is mixed in the already described chemicals. A study has therefore been made also of detection of foreign matter in a supply path for supplying the gas to the processing atmosphere.

The present invention has been made on the basis of such circumstances. It is an object of the present invention to provide a technology that can prevent increases in size and manufacturing cost of a substrate processing apparatus including a plurality of supply paths through which fluids to be supplied to a substrate flow, in a case of detecting foreign matter included in the fluids running through the respective supply paths in the apparatus.

SUMMARY OF THE INVENTION

According to the present invention, there is provided a substrate processing apparatus for processing a substrate by supplying a fluid to the substrate, the substrate processing apparatus including: measurement flow passage portions as part of a respective plurality of supply paths of fluids to be supplied to the substrate, the measurement flow passage portions constituting measurement regions for measurement of foreign matter in the fluids, and being disposed so as to form a row with each other; a light irradiating unit configured to form an optical path in one of the flow passage portions, the light irradiating unit being shared by the plurality of flow passage portions; a moving mechanism configured to move the light irradiating unit relatively along a direction of arrangement of the flow passage portions to form the optical path within the flow passage portion selected among the plurality of flow passage portions; a light receiving unit including a light receiving element, the light receiving element receiving light transmitted by the flow passage portion; and a detecting unit configured to detect foreign matter in the fluid on a basis of a signal output from the light receiving element.

According to the present invention, there is provided a substrate processing method for processing a substrate by supplying a fluid to the substrate, the substrate processing method including: a step of forming an optical path in a flow passage portion by using a light irradiating unit shared by measurement flow passage portions, the measurement flow passage portions being part of a respective plurality of supply paths of fluids to be supplied to the substrate, and the measurement flow passage portions constituting measurement regions for measurement of foreign matter in the fluids and being disposed so as to form a row with each other; a step of moving the light irradiating unit relatively along a direction of arrangement of the flow passage portions by a moving mechanism to form the optical path within the flow passage portion selected among the plurality of flow passage portions; a step of receiving light transmitted by the flow passage portion by a light receiving element included in a light receiving unit; and a step of detecting foreign matter in the fluid by a detecting unit on a basis of a signal output from the light receiving element.

According to the present invention, there are provided a plurality of flow passage portions constituting measurement regions for measurement of foreign matter in fluids and forming a row with each other, a light irradiating unit moved relatively along a direction of arrangement of the flow passage portions to form an optical path within a selected flow passage portion, and a light receiving unit corresponding to the light irradiating unit. Such a configuration enables detection of foreign matter in the fluids in the respective flow passage portions, and can suppress an increase in size of the substrate processing apparatus and an increase in manufacturing cost of the apparatus because the light irradiating unit does not need to be provided for each flow passage portion.

DETAILED DESCRIPTION OF THE INVENTION

Figure 1:
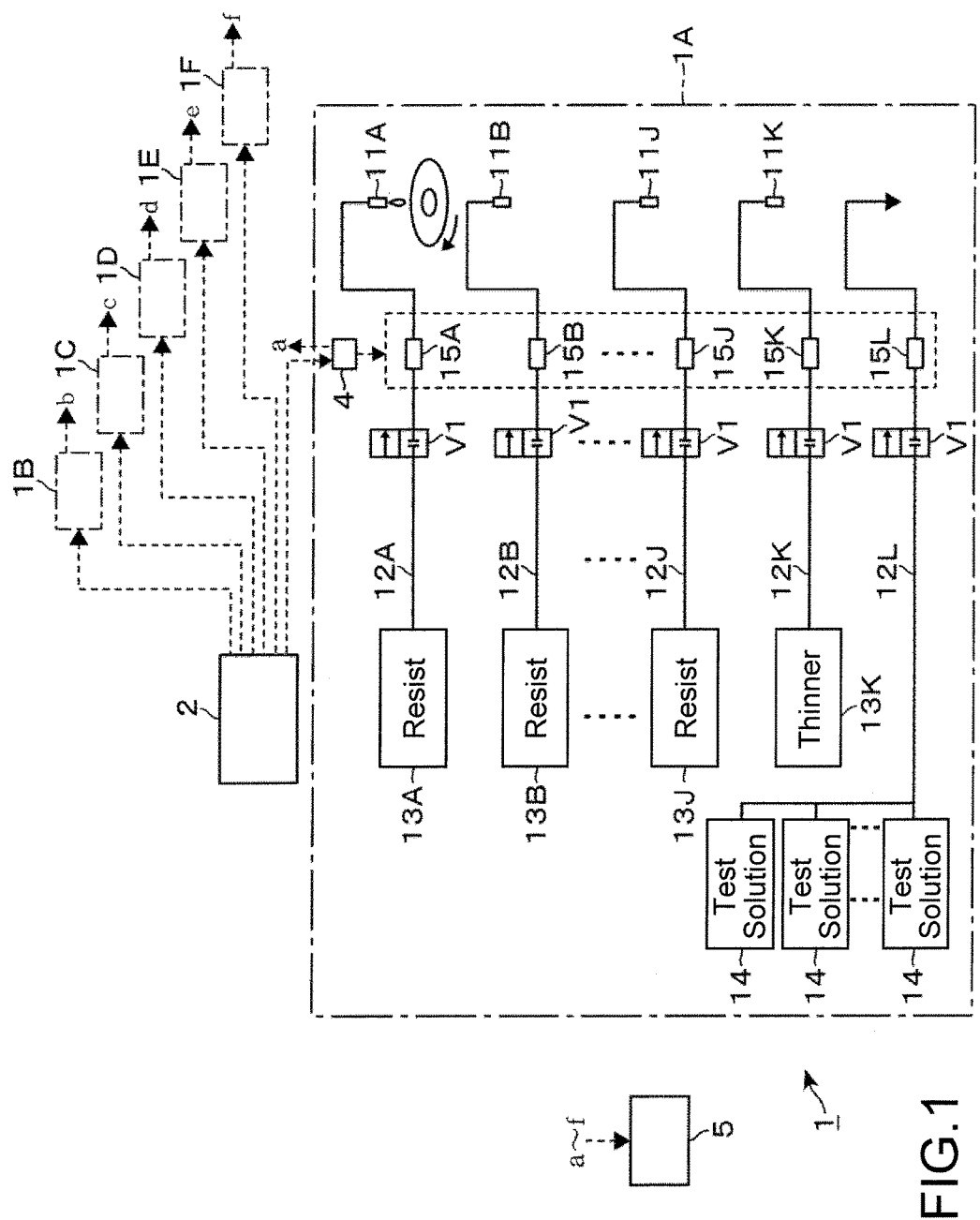
FIG. 1 is a schematic configuration diagram of a coating and developing apparatus according to an embodiment of the present invention.

FIG. 1 is a schematic diagram of a coating and developing apparatus 1 as one embodiment of a substrate processing apparatus to which the present invention is applied. The coating and developing apparatus 1 includes resist coating modules 1A and 1B, antireflection film forming modules 1C and 1D, and protective film forming modules 1E and 1F that supply respective chemicals to a wafer W to process the wafer W. These modules 1A to 1F correspond to the chemical supply devices described in the section of Background Art. The resist coating modules 1A and 1B correspond to the resist coating device described in the section of Background Art. The coating and developing apparatus 1 supplies various kinds of chemicals to the wafer W in these modules 1A to 1F to perform, in order, formation of an antireflection film, formation of a resist film, and formation of a protective film for protecting the resist film at a time of light exposure. The coating and developing apparatus 1 thereafter develops the wafer W that has been exposed to light in an immersed state, for example.

The above-described modules 1A to 1F include a chemical supply path. The coating and developing apparatus 1 is configured to be able to detect foreign matter in a chemical running through the supply path. The chemical that has run through the above-described supply path is supplied to the wafer W. That is, the supply of the chemical to the wafer W and the detection of foreign matter are performed in parallel with each other. The foreign matter is for example particles or air bubbles. The detection of the foreign matter is specifically, for example, the detection of a total number of pieces of foreign matter flowing through a predetermined part in the supply path during a predetermined period and the size of each piece of foreign matter and the determination of the kind of the foreign matter. The determination of the kind of the foreign matter is for example determination of whether the foreign matter is air bubbles or particles.

Figure 2:
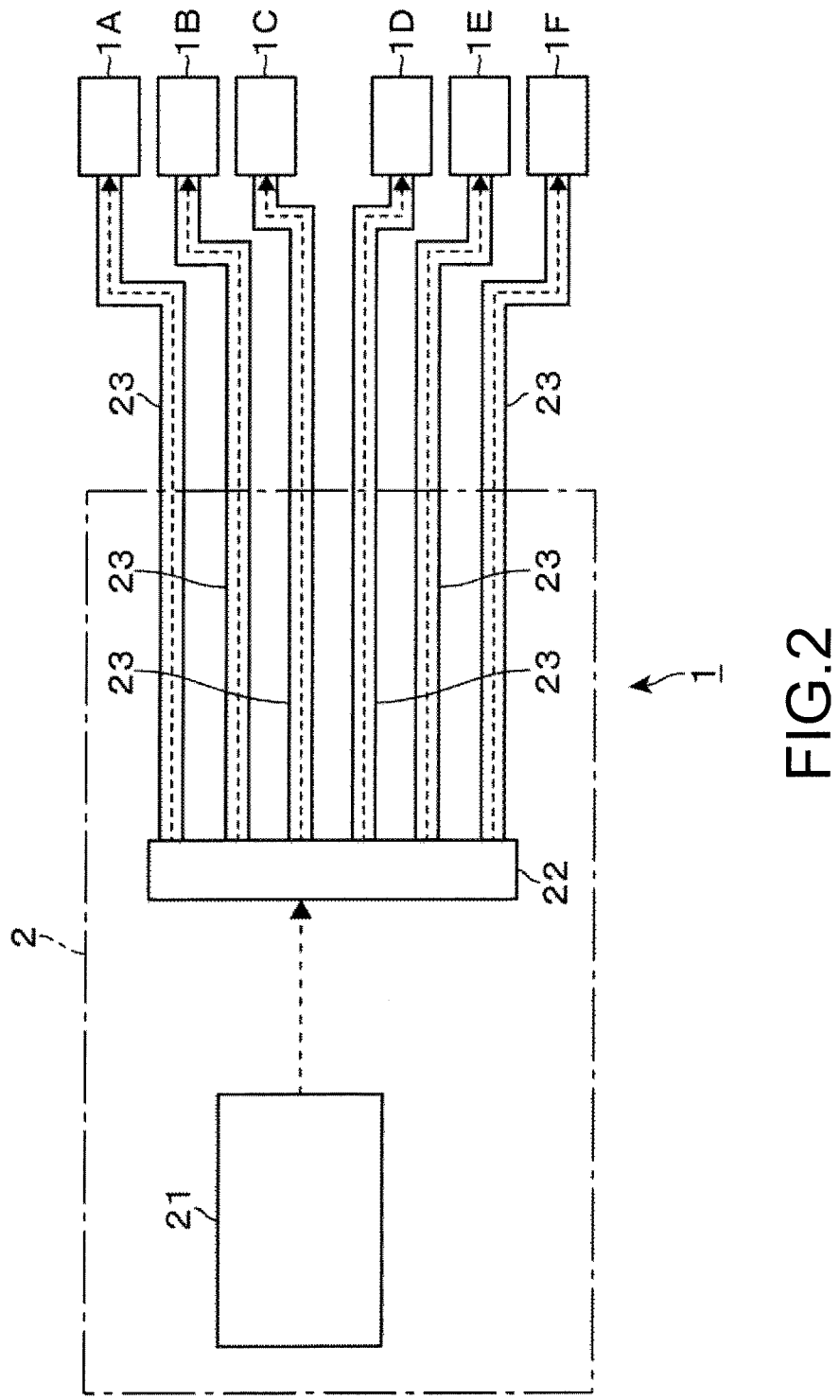
FIG. 2 is a schematic configuration diagram of a light supply unit included in the coating and developing apparatus.

The coating and developing apparatus 1 is provided with a light supply unit 2. FIG. 2 shows a constitution of the light supply unit 2. The light supply unit 2 includes a light source 21 that outputs laser light and a splitter 22 as a split light path forming unit. The splitter 22 divides laser light output from the light source 21 into six pieces of laser light, which are supplied to corresponding foreign matter detecting units 4 provided in the modules 1A to 1F via six fibers 23. Dotted line arrows in FIG. 1 represent the split laser light.

The modules 1A to 1F are configured in a substantially similar manner. The following description will be made of a general configuration of the resist coating module 1A shown in FIG. 1. The resist coating module 1A for example includes 11 nozzles 11A to 11K. Of the 11 nozzles 11A to 11K, 10 nozzles 11A to 11J discharge a resist as a chemical to the wafer W to form a resist film. The nozzle 11K discharges a thinner to the wafer W. The thinner is a pre-wetting chemical that is supplied to the wafer W before being supplied with a resist and which increases the wettability of the resist.

The nozzles 11A to 11J are connected with downstream ends of chemical supply pipes 12A to 12J forming chemical supply paths. Upstream ends of the chemical supply pipes 12A to 12J are respectively connected to resist supply sources 13A to 13J via valves V1. The resist supply sources 13A to 13J include for example bottles storing resists and pumps pumping the resists supplied from the bottles into the nozzles 11A to 11J. The kinds of the resists stored in the respective bottles of the resist supply sources 13A to 13J are different from each other. One kind of resist selected from the 10 kinds of resists is supplied to the wafer W.

The nozzle 11K is connected with a downstream end of the chemical supply pipe 12K. An upstream end of the chemical supply pipe 12K is connected to a supply source 13K via a valve V1. The supply source 13K is formed in a similar manner to the supply sources 13A to 13J except that the supply source 13K stores the above-described thinner in place of the resists. That is, timings in which the chemicals flow through the chemical supply pipes 12A to 12K in processing the wafer W are different from each other. The chemical supply pipes 12A to 12J are formed of a flexible material, for example a resin. The chemical supply pipes 12A to 12J are thus formed so as not to hinder the movement of the nozzles 11A to 11J which movement will be described later.

In addition, the module 1A is provided with a test solution supply pipe 12L formed in a similar manner to the chemical supply pipes 12A to 12K. A downstream end of the test solution supply pipe 12L is for example connected to a drainage path not shown in the figure. An upstream end of the test solution supply pipe 12L is for example branched via a valve V1 into n parts (n is an integer), which are connected to corresponding test solution supply sources 14. Incidentally, n is three or more in FIG. 1, but may be two. The test solution supply sources 14 are different from the resist supply sources 13A to 13J in that the test solution supply sources 14 store test solutions made of pure water in place of the resists. The test solutions include test particles having predetermined particle diameters as foreign matter at predetermined ratios. The particle diameters and ratios of the test particles included in the test solutions differ for the different test solution supply sources 14. Each of the test solutions is used to calibrate reference data used for detection of foreign matter when the processing of the wafer W is not performed, as will be described later.

Cuvettes 15A to 15L are interposed between the nozzles 11A to 11K and the valves V1 in the chemical supply pipes 12A to 12K and on the downstream side of the valve V1 in the test solution supply pipe 12L. The cuvettes 15A to 15K are formed as flow passage portions for measurement of foreign matter. The insides of the cuvettes 15A to 15K form foreign matter measurement regions. The cuvette 15L is formed as a flow passage portion for measurement of the test particles, and forms a region for measurement of the test particles in the test solutions. The cuvettes 15A to 15L will be described later in detail.

Figure 3:
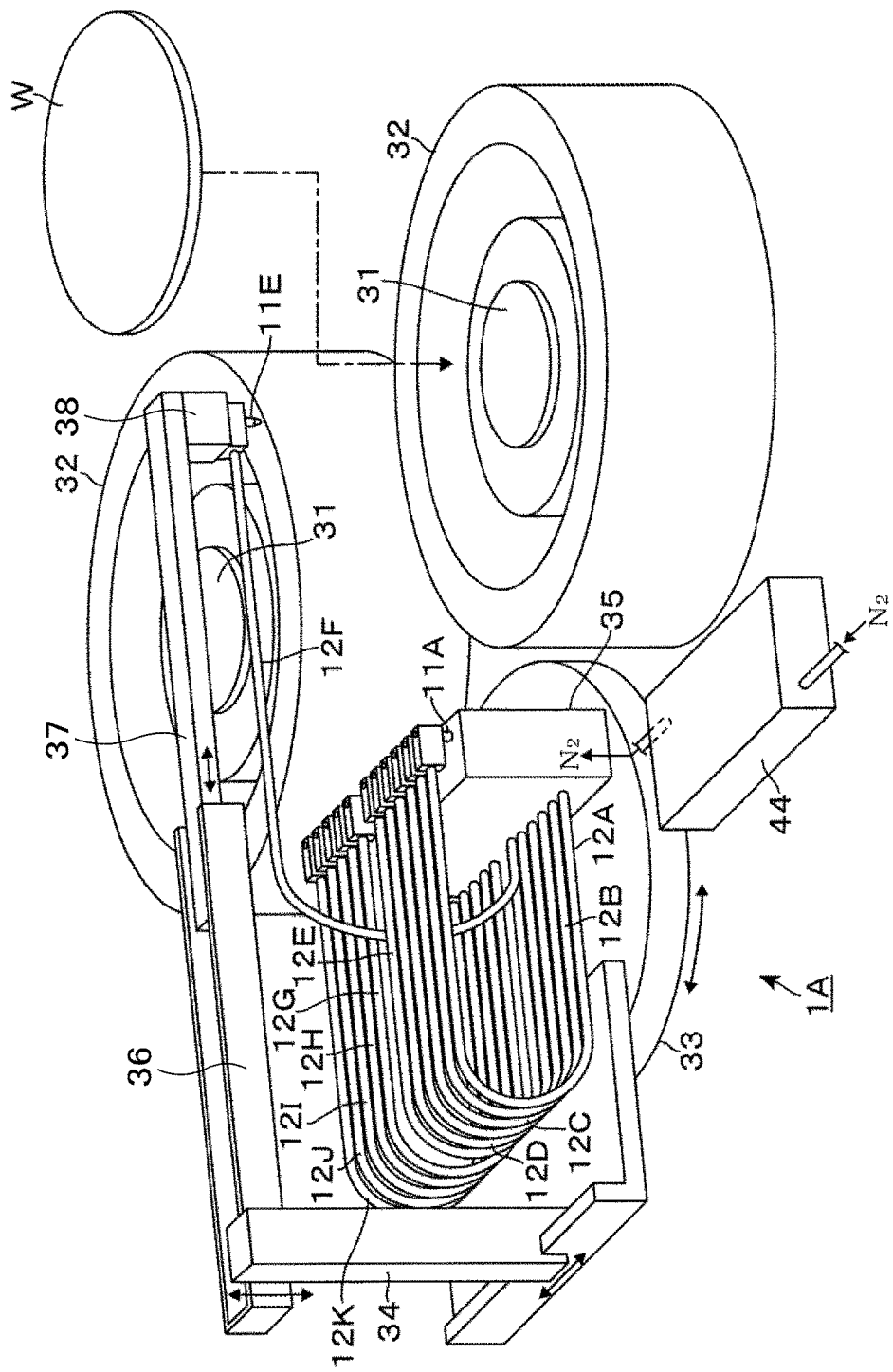
FIG. 3 is a perspective view of a resist coating module included in the coating and developing apparatus.

FIG. 3 shows an example of a more detailed constitution of the resist coating module 1A. Reference numerals 31 and 31 in FIG. 3 denote spin chucks, which each suck and hold a central portion of an undersurface of the wafer W horizontally, and which rotate the held wafer W about a vertical axis. Reference numerals 32 and 32 in FIG. 3 denote cups, which surround a lower part and a side of the wafer W held on the spin chucks 31 to prevent scattering of chemicals.

Reference numeral 33 in FIG. 3 denotes a rotating stage rotating about a vertical axis. Provided on the rotating stage 33 are a vertical column 34 movable horizontally and a holder 35 for the nozzles 11A to 11K. Reference numeral 36 denotes a raising and lowering portion capable of being raised and lowered along the column 34. Reference numeral 37 denotes an arm movable along the raising and lowering portion 36 in a horizontal direction orthogonal to the direction of movement of the column 34. An attaching and detaching mechanism 38 for the nozzles 11A to 11K is provided at an end of the arm 37. Cooperative operation of the rotating stage 33, the column 34, the raising and lowering portion 36, and the arm 37 moves the nozzles 11A to 11K between each spin chuck 31 and the holder 35.

Figure 4:
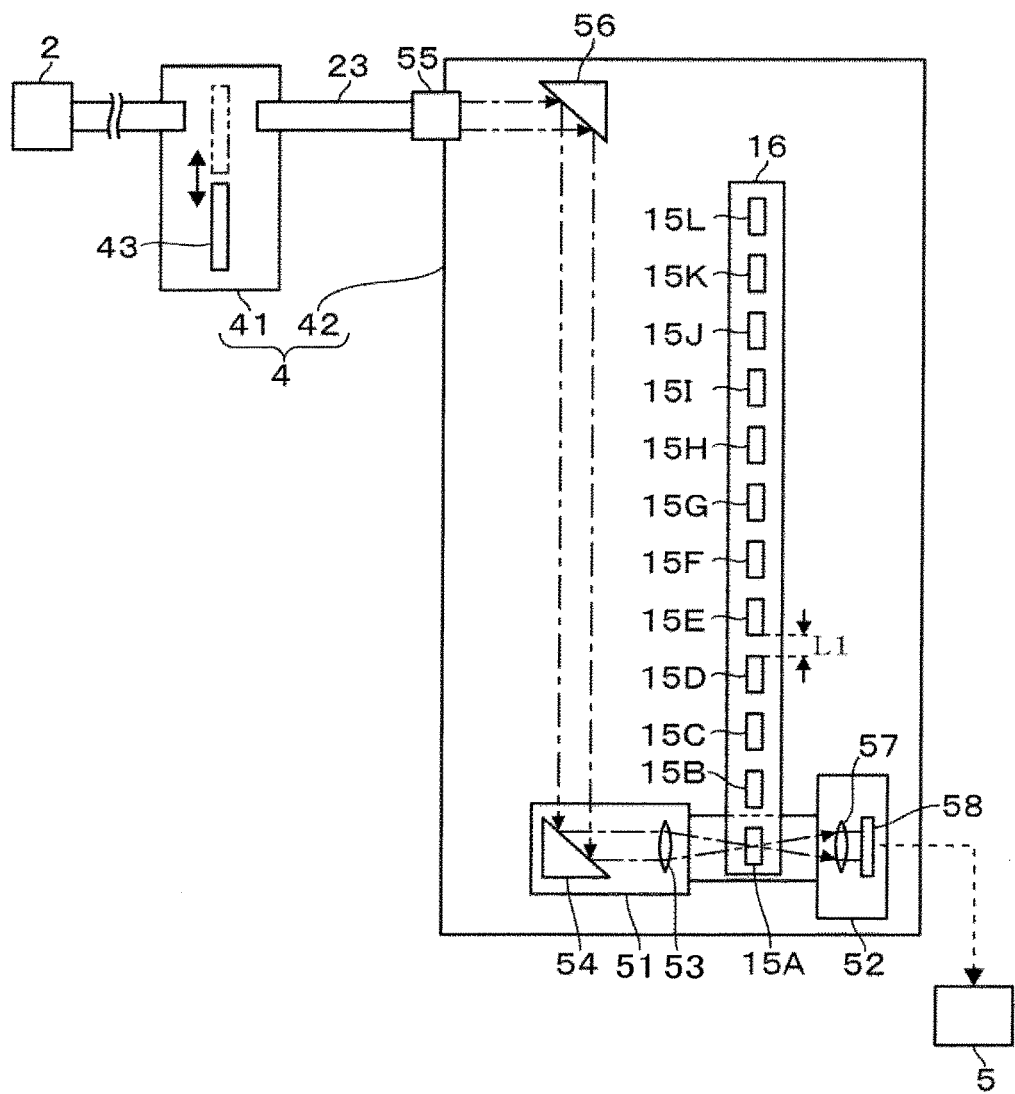
FIG. 4 is a schematic configuration diagram of a foreign matter detecting unit forming a liquid processing system.

FIG. 4 shows a general configuration of the foreign matter detecting unit 4 provided in the resist coating module 1A. The foreign matter detecting unit 4 includes a light supplying and interrupting unit 41 and a detecting unit main body 42. The light supplying and interrupting unit 41 is for example interposed in the already described fiber 23. The light supplying and interrupting unit 41 includes a shutter 43. The shutter 43 opens and closes an optical path between the upstream side and downstream side of the fiber 23 by moving between a shielding position at which the shutter 43 shields the optical path (which shielding position is indicated by a chain double-dashed line in FIG. 4) and an opening position at which the shutter 43 is retracted from the optical path (which opening position is indicated by a solid line in FIG. 4). For example, during the operation of the coating and developing apparatus 1, light is supplied from the light supply unit 2 to the fiber 23 at all times. The shutter 43 opens and closes the optical path, whereby switching is performed between a state in which the light is supplied to the detecting unit main body 42 and a state in which the supply of the light to the detecting unit main body 42 is stopped. A speed at which the shutter 43 moves from one of the shielding position and the opening position described above to the other is for example 100 milliseconds.

The detecting unit main body 42 for example has a casing 44. The casing 44 is provided on the sides of the rotating stage 33 and the cups 32 so as not to interfere with the arm 37 and the column 34 that move. The detecting unit main body 42 includes, within the casing 44, a slider mechanism 45 as a moving mechanism, a light irradiating unit 51, and a light receiving unit 52. Description will be made referring also to FIG. 5, which is a perspective view showing in detail a constitution within the casing 44. The already described supply pipes 12A to 12L are routed within the casing 44, and the cuvettes 15A to 15L are arranged within the casing 44. The cuvettes 15A to 15L are formed so as to be similar to each other as elongate erected tubes.

In addition, the cuvettes 15A to 15L are formed of a transparent quartz, for example, to be able to transmit light guided from the light supply unit 2 to the detecting unit main body 42. The cuvettes 15A to 15L are arranged in a row so as to be in proximity to each other in the horizontal direction, thus forming a flow passage array 16. An interval of cuvettes 15 adjacent to each other, which interval is indicated as L1 in FIG. 4, for example, is 10 mm or less.

Figure 5:
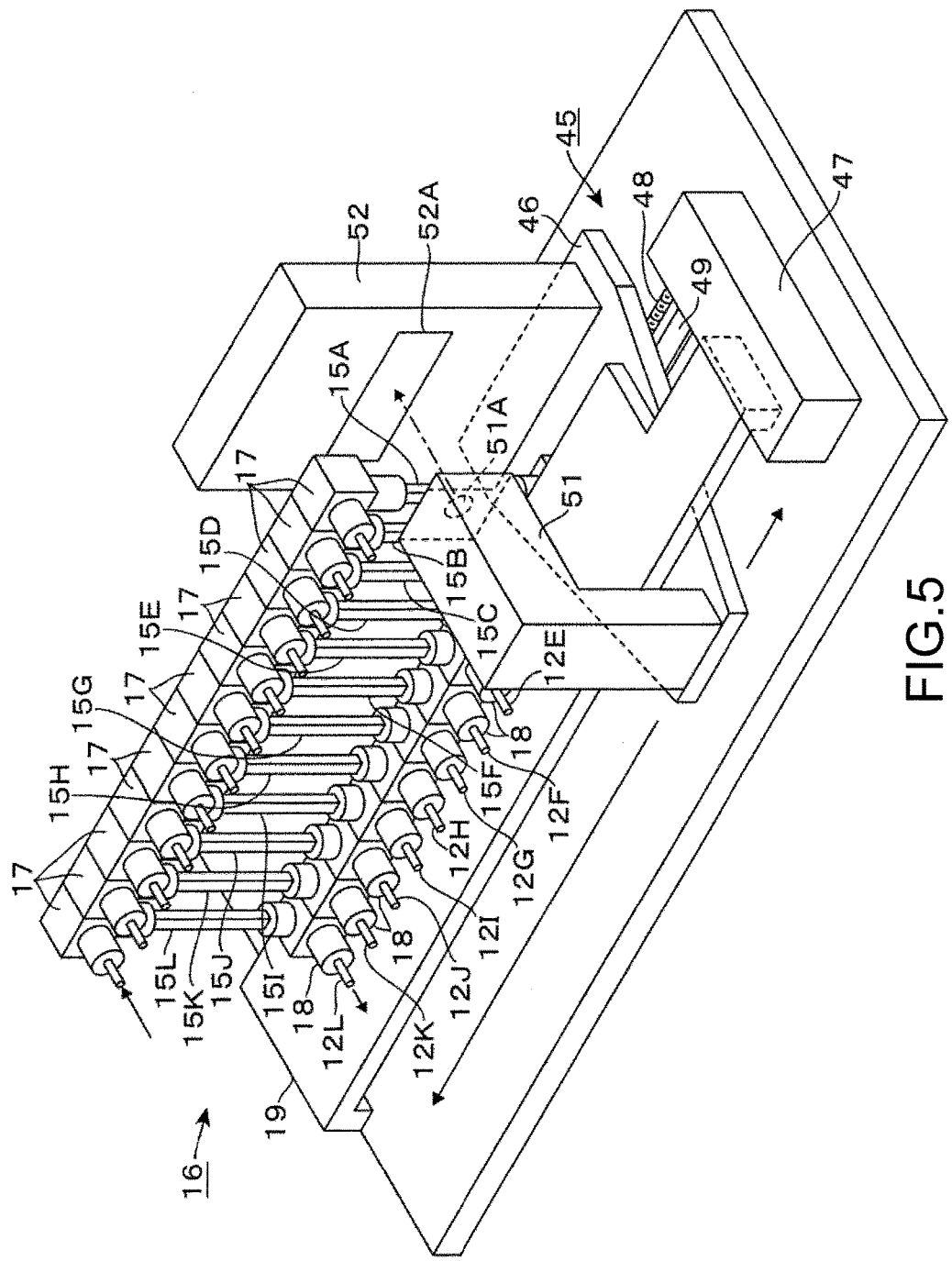
FIG. 5 is a perspective view of a detecting unit main body forming the foreign matter detecting unit.

Reference numerals 17 and 18 in FIG. 5 denote joints for respectively connecting the upstream sides and the downstream sides of the cuvettes 15A to 15L to the supply pipes 12A to 12L. The cuvettes 15A to 15L and the joints 17 and 18 are provided on a support 19. The above-described slider mechanism 45 includes, for example, a moving base 46 provided below the support 19, a driving mechanism 47 including a motor, a ball screw 48 that is connected to the moving base 46 and which moves the moving base 46 by being rotated by the driving mechanism 47, and a rail 49 that guides the movement of the moving base 46. Such a constitution enables the moving base 46 to be moved horizontally along the direction of arrangement of the cuvettes 15A to 15L. The light irradiating unit 51 and the light receiving unit 52 are provided on the moving base 46 so as to sandwich the cuvettes 15A to 15L from sides and so as to face each other.

The light irradiating unit 51 constitutes an optical system for light irradiation. As shown in FIG. 4, the light irradiating unit 51 includes an objective lens 53 as a condensing lens and a moving mirror 54. A collimator 55 forming the downstream end of the fiber 23 and a fixed mirror 56 are provided within the casing 44. Collimated light having a beam diameter of 7 mm, for example, is applied horizontally from the collimator 55 to the fixed mirror 56. Then, the light reflected by the fixed mirror 56 is applied horizontally to the moving mirror 54 of the above-described light irradiating unit 51 along the direction of arrangement of the cuvettes 15A to 15L. Further, this light is reflected by the moving mirror 54, and applied horizontally to one of the cuvettes 15A to 15L via the objective lens 53. Incidentally, FIG. 5 shows neither of the collimator 55 and the fixed mirror 56.

The light receiving unit 52 constitutes an optical system for receiving light. The light receiving unit 52 includes a lens 57 for receiving light and a light receiving element 58 formed by a photodiode, for example. The light applied from the light irradiating unit 51 to one of the cuvettes 15A to 15L is guided to the light receiving element 58 via the light receiving lens 57. Receiving this light, the light receiving element 58 outputs an electric signal to a control unit 5 to be described later. Supposing that the direction of light irradiation of the light irradiating unit 51 is a front-rear direction, the respective focuses of the objective lens 53 and the light receiving lens 57 are positioned at a central portion in the front-rear direction of each of the cuvettes 15A to 15L. Incidentally, reference numerals 51A and 52A in FIG. 5 denote opening portions that are provided in the light irradiating unit 51 and the light receiving unit 52, respectively, and through which the light applied from the objective lens 53 to a cuvette 15 and the light transmitted by the cuvette 15 pass, respectively.

Figure 6:
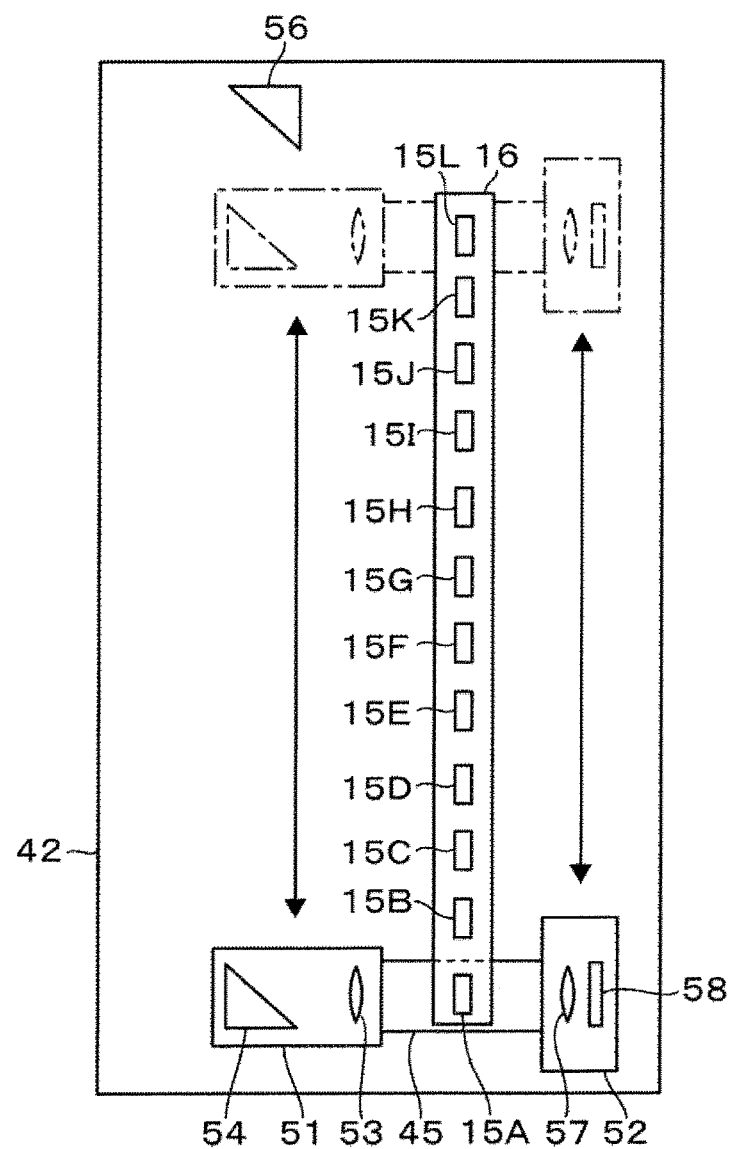
FIG. 6 is a diagram of assistance in explaining movement of parts in the detecting unit main body.

As shown in FIG. 6, the slider mechanism 45 can move the light irradiating unit 51 and the light receiving unit 52 to such a position as to sandwich an arbitrary cuvette 15 of the cuvettes 15A to 15L. Then, as a result of such a movement, the respective focuses of the objective lens 53 and the light receiving lens 57 are positioned at a central portion in a left-right direction of the arbitrary cuvette 15 (direction of arrangement of the cuvettes 15A to 15L). Then, in the state in which the focuses are thus positioned, the light irradiating unit irradiates the light receiving unit 52 with light via the cuvette 15. An optical path that passes through the cuvette 15 is thus formed between the light irradiating unit 51 and the light receiving unit 52.

Because the moving mirror 54 is located at the position corresponding to the cuvette 15 irradiated with light, a distance between the moving mirror 54 and the fixed mirror 56 differs at times of irradiation of the different cuvettes 15A to 15L with light. However, due to the above-described collimator 55, the light between these mirrors 54 and 56 is collimated light. Therefore, even when the distance between the mirrors 54 and 56 thus differs, variations in the light guided to the objective lens 53 are suppressed. Hence, a similar optical path is formed between the light irradiating unit 51 and the light receiving unit 52 when light is applied from the light irradiating unit 51 to each of the cuvettes 15A to 15L. Representatively, alternate long and short dashed lines in FIG. 4 schematically represent the optical path formed through the cuvette 15A. The light irradiation from the light irradiating unit 51 is performed while a liquid is running through the cuvette 15 to be irradiated with light. The control unit 5 to be described later obtains a signal output from the light receiving element 58 during the light irradiation.

When foreign matter is included in the liquid running through the cuvette 15 irradiated with light from the light irradiating unit 51, and is positioned on the optical path, the signal output from the light receiving element 58 changes according to the size of the foreign matter. In addition, the signal output at this time is in accordance with the type of the foreign matter. Hence, the output signal from the light receiving element 58 includes information about the particle diameter of the foreign matter blocking the light, the number of pieces of the foreign matter, and the type of the foreign matter. The control unit 5 can detect the number of pieces of the foreign matter and the size of the foreign matter and determine the type of the foreign matter on the basis of the output signal. It is to be noted that cases where only one of the detection of the number of pieces of the foreign matter, the detection of the size of the foreign matter, and the determination of the type of the foreign matter is performed as foreign matter detection, for example cases where only the determination of the type of the foreign matter is made are included in the scope of rights of the present invention. The detection of the number of pieces of the foreign matter and the size of the foreign matter and the determination of the type of the foreign matter on the basis of the output from the light receiving element 58 may be performed by using for example an IPSA (registered trademark) method of PML (Particle Monitoring Technologies Ltd.), or may be based on a light scattering method.

To supplementarily describe the casing 44 described above, a N2 gas is supplied to the inside of the casing 44 and is exhausted from the inside of the casing 44, as shown in FIG. 3, in order to prevent the chemical discharged and scattered from each of the nozzles 11A to 11K from entering the inside of the casing 44 described above, and thus prevent the chemicals from affecting the respective operations of the driving mechanism 47, the light receiving unit 52, and the like. However, the N2 gas may not be supplied and exhausted when another measure is taken to prevent each part within the casing 44 from being covered with the liquids.

To describe the modules other than the resist coating module 1A, the resist coating module 1B is configured in a similar manner to the module 1A. The antireflection film forming modules 1C and 1D and the protective film forming modules 1E and 1F are configured in a similar manner to the modules 1A and 1B except that the antireflection film forming modules 1C and 1D and the protective film forming modules 1E and 1F supply chemicals for forming an antireflection film and chemicals for forming a protective film, respectively, in place of the resists and the thinner, for example. For example, also in the modules 1C to 1F, as in the modules 1A and 1B, one chemical selected from a plurality of chemicals is supplied to the wafer W.

Description will next be made of the control unit 5 provided to the coating and developing apparatus 1. The control unit 5 is formed by a computer, for example. The control unit 5 has a program storage unit not shown in the figures. The program storage unit stores a program in which instructions (step group) are constructed so as to perform the respective operations of the processing of the wafer W and the detection of the foreign matter in each module, the transfer of the wafer W within the coating and developing apparatus 1 by a transfer mechanism to be described later, and the like. A control signal is output from the control unit 5 to each part of the coating and developing apparatus 1 according to the program, whereby each of the above-described operations is performed. This program is for example stored in the program storage unit in a state of being stored on a storage medium such as a hard disk, a compact disk, a magneto-optical disk, a memory card, or the like.

In addition, a memory included in the control unit 5 stores reference data for detecting the above-described foreign matter. This reference data includes a first correspondence relation that defines relation between the output signal from the light receiving element 58 and the particle diameter of the foreign matter to calculate the particle diameter on the basis of the output signal. As described above, the focus of the objective lens 53 is at the central portion in each of the front-rear direction and the left-right direction of a cuvette 15. The optical path is therefore formed in a limited region within the cuvette 15. Hence, foreign matter running through only a part of the cuvette 15 is positioned on the optical path, and detected. The above-described reference data includes second correspondence relation that defines relation between the number of pieces of the foreign matter thus flowing through the part of the cuvette 15 and detected for each particle diameter of the foreign matter and the number of pieces of the foreign matter actually flowing through the whole of the cuvette 15 to calculate the number of pieces of the foreign matter flowing through the whole of the cuvette 15 for each particle diameter of the foreign matter. The reference data is set for each of the modules 1A to 1F, and is calibrated individually. This calibration will be described later.

The processing of the wafer W and the detection of the foreign matter, which are performed in the above-described resist coating module 1A, will next be described with reference to a timing chart of FIG. 7. This timing chart shows timing in which a pressure of the pump in one supply source 13 of the supply sources 13A to 13L is set, timing in which the light irradiating unit 51 and the light receiving unit 52 are moved, timing in which the valve V1 of the supply pipe 12 corresponding to the one supply source 13 among the supply pipes 12A to 12L is opened and closed, timing in which switching is performed between a state of laser light being applied from the light irradiating unit 51 and a state of the application of the laser light being stopped, and timing in which the control unit 5 obtains a signal from the light receiving element 58. The above-described timing in which switching is performed between the state of the laser light being applied and the state of the application being stopped can also be said to be timing in which the shutter 43 of the foreign matter detecting unit 4 is opened and closed.

First, the wafer W is transferred onto the spin chuck 31 by a transfer mechanism F3 to be described later that is provided to the coating and developing apparatus 1. The wafer W is then held on the spin chuck 31. The arm 37 transfers the nozzle 11K for supplying the thinner to a position above the wafer W, and the pump of the supply source 13K sucks the thinner, whereby a setting is started so as to achieve a predetermined pressure (time t1). In addition, together with the start of the setting of the pump, the light irradiating unit 51 and the light receiving unit 52 start to be moved toward positions that sandwich the cuvette 15K. At this time, the shutter 43 of the foreign matter detecting unit 4 is closed.

The light irradiating unit 51 and the light receiving unit 52 are stopped at the positions sandwiching the cuvette 15K (time t2). Next, the valve V1 of the supply pipe 12K is opened. The thinner is pumped from the pump toward the nozzle 11K at a predetermined flow rate. In addition, the shutter 43 is opened, and light is applied from the light irradiating unit 51, so that an optical path passing through the cuvette 15K is formed between the light irradiating unit 51 and the light receiving unit 52 (time t3). Then, the pumped thinner passes through the cuvette 15K, and is discharged from the nozzle 11K to the central portion of the wafer W. When a degree of opening of the valve V1 has increased to reach a predetermined degree of opening, the increase in the degree of opening is stopped (time t4). The control unit 5 then starts to obtain an output signal from the light receiving element 58 (time t5). Thereafter, the control unit 5 stops obtaining the output signal (time t6). Next, the shutter 43 is closed to stop the light irradiation from the light irradiating unit 51, and the valve V1 of the supply pipe 12K is closed (time t7), so that the discharge of the thinner to the wafer W is stopped. The wafer W is then rotated. The thinner is expanded to the periphery of the wafer W by a centrifugal force.

On the basis of the output signal obtained during the period of time t5 to t6 and the reference data, a total number of pieces of the foreign matter running through the cuvette 15K during the period of time t5 to t6 and the particle diameter of each piece of the foreign matter are calculated, and the type of the foreign matter is determined. Thereafter, determination of whether or not the calculated total number of pieces of the foreign matter is a threshold value or more and determination of whether or not the number of pieces of foreign matter larger than a predetermined particle diameter is a threshold value or more are made for each type of the foreign matter, for example. Then, when it is determined that the above-described total number of pieces of the foreign matter is the threshold value or more, and/or when it is determined that the number of pieces of foreign matter larger than the predetermined particle diameter is the threshold value or more, an alarm is output, and the module 1A stops operating, so that the processing of the wafer W is stopped. Specifically, this alarm is for example a predetermined display on a monitor forming the control unit 5 or the output of a predetermined sound from a speaker forming the control unit 5. In addition, the output of the alarm includes for example display or sound output for notifying a user of the cuvette 15 in which an abnormality is detected among the cuvettes 15A to 15K and the detected type of the foreign matter.

When it is determined that the total number of pieces of the foreign matter is not the threshold value or more, and it is determined that the number of pieces of foreign matter larger than the predetermined particle diameter is not the threshold value or more, no alarm is output, and the module 1A does not stop operating. Incidentally, each of the calculations and the determinations is performed by the control unit 5. In addition, even when the result of determination of the calculated total number of pieces of the foreign matter and the calculated number of pieces of foreign matter larger than the predetermined particle diameter does not indicate an abnormality, the user may be notified, by the screen display or the audio output described above, of the detected types of the foreign matter, the total number of pieces of the foreign matter for each type and/or the number of pieces of foreign matter larger than the predetermined particle diameter for each type, for example. Incidentally, the determination of whether or not the calculated total number of pieces of the foreign matter is the threshold value or more and the determination of whether or not the number of pieces of foreign matter larger than the predetermined particle diameter is the threshold value or more are not limited to being made for each type of the foreign matter, as described above, but may be made by comparing, with threshold values, a total number of pieces of foreign matter of all of types and the number of pieces of foreign matter all of the types which pieces have particle diameters equal to or more than a predetermined size.

Figure 7:
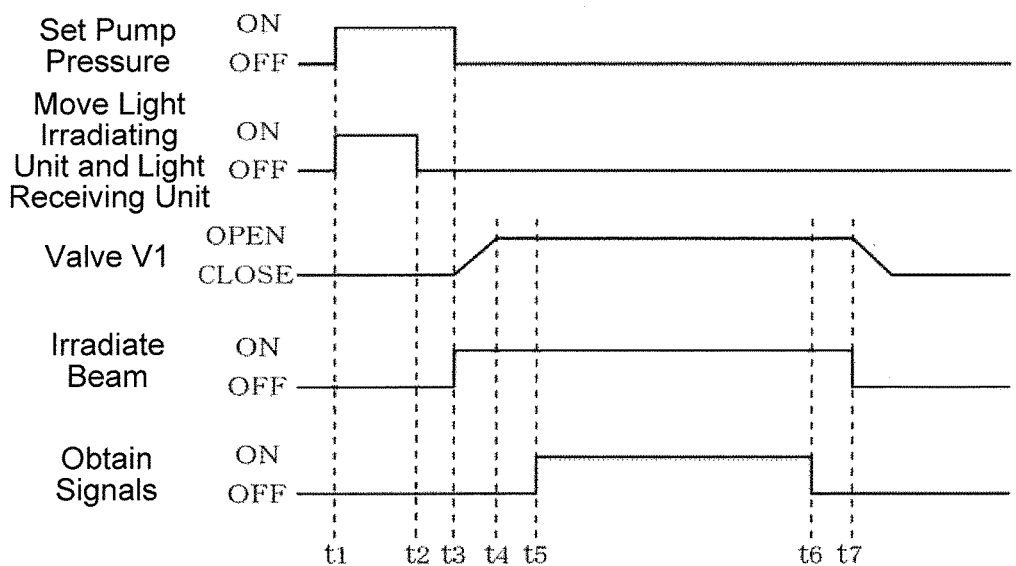
FIG. 7 is a timing chart of operation of parts in the resist coating module.

Next, the discharge of a resist to the wafer W and the detection of foreign matter in the resist are performed along the timing chart of FIG. 7 as in the discharge of the thinner and the detection of the foreign matter in the thinner as described above. When description is made supposing that the resist of the supply source 13A, for example, is discharged to the wafer W, the nozzle 11A is moved to a position above the wafer W coated with the thinner, and a pressure of the pump of the supply source 13A is set (time t1). Meanwhile, the light irradiating unit 51 and the light receiving unit 52 start to be moved to positions sandwiching the cuvette 15A (time t2), and are stopped at the positions. Thereafter, the valve V1 of the supply pipe 12A is opened to pump the resist from the pump to the nozzle 11A, and the shutter 43 is opened to form an optical path between the light irradiating unit 51 and the light receiving unit 52 via the cuvette 15A (time t3).

After the resist passes through the cuvette 15A and is discharged to the central portion of the wafer W, and a degree of opening of the valve V1 reaches a predetermined degree of opening (time t4), the obtainment of an output signal from the light receiving element 58 is started (time t5). After the obtainment of the output signal is stopped (time t6), the shutter 43 is closed, and the valve V1 is closed to stop the discharge of the resist to the wafer W (time t7). The wafer W is rotated, and the resist is expanded to the periphery of the wafer W by a centrifugal force, so that a resist film is formed. While the resist film is thus formed, a total number of pieces of foreign matter running through the cuvette 15A during the period of time t5 to t6 and the particle diameter of each piece of foreign matter are calculated on the basis of the output signal obtained during the period of time t5 to t6 and the reference data, and whether or not these calculated values are threshold values or more as described above are determined. Then, depending on a result of the determination, an alarm may be output, and the operation of the module may be stopped, as already described.

When the resists included in the supply sources other than the supply source 13A are discharged to the wafer W, operation similar to that in the case of performing coating with the resist of the supply source 13A in the resist coating module 1A is performed except that the pumps of the supply sources different from the supply source 13A operate, the valves V1 of the supply pipes different from the supply pipe 12A are opened and closed, and the cuvettes different from the cuvette 15A are irradiated with light.

Incidentally, the output of the alarm and the stopping of the operation of the module as already described are not limited to being performed on the basis of a result of one measurement. For example, each time the discharge of a chemical to the wafer W and the detection of foreign matter are performed as described above, a calculated total number of pieces of the foreign matter and the number of pieces of foreign matter larger than the predetermined particle diameter are stored in the memory of the control unit 5 for each cuvette 15 in which the foreign matter is detected. Then, for one cuvette 15, moving averages of the newly obtained measured values and measured values in a predetermined number of measurements, the measured values in the predetermined number of measurements having been obtained in the past, are calculated, and the calculated moving average values may be compared with threshold values to make each of the above-described determinations. In addition, integrated values of the newly obtained measured values and measured values in a predetermined number of measurements, the measured values in the predetermined number of measurements having been obtained in the past, may be compared with threshold values to make the above-described determinations.

In the foreign matter detection described with reference to the chart of FIG. 7, the timings in which the valve V1 is opened and closed and the timings in which the control unit 5 starts and ends the obtainment of the output signal are shifted from each other as described above in order to increase accuracy of measurement by performing the foreign matter detection in a state in which a liquid flow in the cuvette 15J is stable. For example, the period of time t4 to t5 is 10 milliseconds to 1000 milliseconds, and the period of time t6 to t7 is 10 milliseconds to 100 milliseconds.

Description will next be made of the calibration of the reference data which calibration is performed in the resist coating module 1A. This calibration is performed to make the already described foreign matter detection with high accuracy even after occurrence of a secular change in the optical system due to a degradation in an antireflection film provided to the surfaces of the lenses 53 and 57 or the like, a decrease in the intensity of the light source 21, a decrease in sensitivity of the light receiving element 58, and the like. An operation of the module 1A for performing the calibration is automatically performed while the module 1A is in a standby state without the wafer W having been transferred to the module 1A, for example. However, the operation of the module 1A for performing the calibration is not limited to such timing, but may be performed at a time of a start-up after power to the coating and developing apparatus 1 is turned on or in arbitrary timing specified by the user of the coating and developing apparatus 1.

A procedure for the calibration will be described in the following. For example, the light irradiating unit 51 and the light receiving unit 52 are moved to positions sandwiching the cuvette 15L. A test solution is supplied from a test solution supply source (assumed to be a first test solution supply source) 14 to the cuvette 15L. An optical path is formed between the light irradiating unit 51 and the light receiving unit 52 so as to pass through the cuvette 15L while the test solution runs through the cuvette 15L. An output signal from the light receiving element 58 is obtained.

Next, a test solution is supplied from a test solution supply source (assumed to be a second test solution supply source) 14 different from the first test solution supply source 14 to the cuvette 15L at a predetermined flow rate. Then, as in the case where the test solution is supplied from the first test solution supply source 14, the cuvette 15L is irradiated with light, and an output signal from the light receiving element 58 is obtained. Thereafter, test solutions are supplied in order from test solution supply sources 14 different from each other at the predetermined flow rate. Each time a test solution is supplied to the cuvette 15L, an optical path is formed so as to pass through the cuvette 15L, and an output signal from the light receiving element 58 is obtained. Thus, the test solutions are supplied from all of the n test solution supply sources 14 to the cuvette 15L, and the signals from the light receiving element 58 are obtained. The supply of the test solutions to the cuvette 15L, the light irradiation from the light irradiating unit 51, and the obtainment of the output signals are performed along the timing chart of FIG. 7 as in the already described detection of foreign matter in the thinner and the resists.

The particle diameter of test particles as foreign matter included in each test solution is known. Thus, on the basis of each output signal obtained while each test solution is supplied to the cuvette 15L, the control unit 5 can obtain the already described first correspondence relation, which is relation between the output signal and the particle diameter of the foreign matter. Moreover, in addition to the particle diameter, a ratio of the test particles included in each test solution is known, and the test solution flows through the cuvette 15L having a fixed volume at a predetermined flow rate. Therefore, on the basis of the ratio of the included test particles, the control unit 5 can calculate a total number of test particles flowing through the cuvette 15L while the output signal from the light receiving element 58 is obtained. Further, the control unit 5 can detect the number of test particles positioned on the optical path while obtaining the output signal, as already described. Hence, the control unit 5 can obtain the above-described second correspondence relation, which is correspondence relation between the number of pieces of foreign matter flowing on the optical path and detected and the total number of pieces of foreign matter flowing through the whole of the cuvette 15L for each particle diameter of the foreign matter. Incidentally, as for correspondence relation between foreign matter having a particle diameter which foreign matter is not supplied to the cuvette 15L and an output signal obtained from the foreign matter having the particle diameter, the first correspondence relation and the second correspondence relation described above are obtained by calculation according to a predetermined algorithm from correspondence relation between foreign matter having a known particle diameter which foreign matter is supplied to the cuvette 15L and the output signal obtained from the foreign matter having the particle diameter, as described above.

When the first correspondence relation and the second correspondence relation as the reference data are thus obtained, the reference data within the memory is calibrated into the newly obtained reference data. The detection of foreign matter which detection is to be subsequently performed at times of discharge of the resists and the thinner in the resist coating module 1A is performed on the basis of the calibrated reference data. Incidentally, the obtainment and calibration of the above-described reference data are performed by the control unit 5. The operation of the module 1A has been described representatively. As with the module 1A, the other modules perform the supply of chemicals and the detection of foreign matter as well as the calibration of the reference data.

In the modules 1A to 1F provided to the coating and developing apparatus 1, the cuvettes 15A to 15K are interposed in the chemical supply pipes 12A to 12K connecting the chemical supply sources 13A to 13K to the nozzles 11A to 11K, and the cuvettes 15A to 15K are arranged in proximity to each other. The light irradiating unit 51 and the light receiving unit 52 are configured to be movable in the direction of arrangement of the cuvettes 15. According to timing in which a chemical is discharged from one nozzle 11 of the nozzles 11A to 11K, an optical path is formed between the light irradiating unit 51 and the light receiving unit 52 so as to pass through the cuvette 15 corresponding to the nozzle, and foreign matter is detected optically. Because the cuvettes 15A to 15K are thus in proximity to each other, and further the light irradiating unit 51 and the light receiving unit 52 are shared by each cuvette 15, it is possible to suppress an increase in size of each of the modules 1A to 1F, and suppress an increase in manufacturing cost. In addition, the cuvette 15L through which the test solutions for calibrating the data for the foreign matter detection run is also provided in proximity to the cuvettes 15A to 15K, and the light irradiating unit 51 and the light receiving unit 52 are also shared with the cuvette 15L. Thus, an increase in size of the modules 1A to 1F is suppressed also in this respect.

In addition, when foreign matter is thus detected, cleanliness of a chemical supplied to the wafer W is monitored. When the cleanliness of the chemical is decreased from a predetermined reference, the operation of the module is stopped as described above, and thereby the processing of subsequent wafers W in the module is stopped. Hence, a chemical having low cleanliness is prevented from being supplied to the subsequent wafers W. A decrease in yield can therefore be prevented. Further, a supply pipe 12 in which foreign matter is detected among the chemical supply pipes 12A to 12K is identified. The user of the coating and developing apparatus 1 can therefore immediately perform maintenance or repair after the operation of the module is stopped. Hence, a time during which the operation of the module is stopped is reduced. It is therefore possible to prevent a decrease in productivity for semiconductor products in the coating and developing apparatus 1.

The valves V1 and the pumps described above can be a source of foreign matter. Therefore, the above-described chemical supply pipes 12A to 12K are provided with the cuvettes 15A to 15K on the downstream side of the valves V1 and the pumps to detect foreign matter in the chemicals discharged to the wafer W with high accuracy. However, the chemical supply pipes 12A to 12K may be provided with the cuvettes 15A to 15K on the upstream side of the valves V1 or pumps to detect foreign matter.

In addition, in the above-described modules 1A to 1F, the collimator 55 is used to irradiate each of the cuvettes 15A to 15L with light in a similar manner. Thus, variations in detection accuracy between the cuvettes 15A to 15K are suppressed, and the already described calibration can be performed with higher accuracy. However, without the collimator 55 being thus provided, the downstream end of the fiber 23, for example, may be connected to the light irradiating unit 51, and light may be directly guided from the downstream end to the lens 53. Therefore, the optical system for light irradiation which optical system is moved along the direction of arrangement of the cuvettes 15 is not limited to combinations of members such as lenses, reflecting mirrors, prisms, and the like for effecting convergence, divergence, reflection, refraction, and the like of light, but may be formed by one lens. Similarly, the optical system for light reception which optical system is moved along the direction of arrangement of the cuvettes 15 may be formed by only one lens 57 without including a reflecting mirror or the like.

In addition, when the supply pipes 12A to 12L are formed of a material capable of transmitting light from the light irradiating unit 51 instead of interposing the cuvettes 15 in the supply pipes 12A to 12L, an optical path can be formed between the light irradiating unit 51 and the light receiving unit 52 so as to pass through the supply pipes 12A to 12L to detect foreign matter. That is, the cuvettes 15A to 15L do not need to be provided. Further, in the above-described module 1A, instead of moving the light irradiating unit 51 and the light receiving unit 52 with respect to the flow passage array 16, the slider mechanism 45 may be configured such that the flow passage array 16 is moved with respect to the light irradiating unit 51 and the light receiving unit 52. Incidentally, in the above-described module 1A, for example, the light receiving unit 52, for example, may be configured to be individually provided for each of the cuvettes 15, and not to be moved with respect to the cuvettes 15.

Further, action to be taken when it is determined that the total number of pieces of the foreign matter running through the cuvette 15 is the threshold value or more and/or when it is determined that the number of pieces of foreign matter larger than the predetermined particle diameter is the threshold value or more, as described above, is not limited to the output of an alarm and the stopping of the operation of the module. For example, the chemical supply source 13 corresponding to the cuvette 15 for which such determinations are made supplies the nozzle 11 with the chemical as a cleaning solution for the supply pipe 12 to remove the foreign matter included in the chemical supply pipe 12 from the nozzle 11. That is, the supply pipe 12 is cleaned automatically. Processing of subsequent wafers W may be resumed after the operation.

In the case where the supply pipe 12 is thus cleaned, during the supply of the cleaning solution to the nozzle, the cuvette 15 may be irradiated with light, and the control unit 5 may determine whether or not the total number of pieces of foreign matter is the threshold value or more and determine whether or not the number of pieces of foreign matter larger than the predetermined particle diameter is the threshold value or more, as in the processing performed by supplying a chemical to the wafer W. Then, depending on a result of these determinations, the control unit 5 may determine whether to continue the cleaning of the chemical supply pipe 12 or to end the cleaning of the chemical supply pipe 12.

A modification of the detecting unit main body 42 will next be described with reference to FIG. 8. In the present example, moving bases 64 and 65 and slider mechanisms 66 and 67 constituting a lens displacing mechanism are provided on a moving base 46 moved in the direction of arrangement of the cuvettes 15 described above. As with the slider mechanism 45, the slider mechanisms 66 and 67 include for example a motor, a ball screw, and a guide rail. The slider mechanisms 66 and 67 move the respective moving bases 64 and 65 horizontally in a front-rear direction. A light irradiating unit 51 and a light receiving unit 52 are provided on the moving bases 64 and 65, respectively. That is, the slider mechanisms 66 and 67 respectively move the light irradiating unit 51 and the light receiving unit 52 in the front-rear direction (optical path direction).

Reasons that the light irradiating unit 51 and the light receiving unit 52 are configured so as to be thus movable will be described. As described above, kinds of chemicals different from each other run through the respective cuvettes 15. Because the kinds are thus different from each other, indexes of refraction of the respective chemicals may be different from each other. In that case, when the positions in the front-rear direction of the light irradiating unit 51 and the light receiving unit 52 are fixed, the positions of the focuses of the objective lens 53 and the light receiving lens 57 may be shifted in the front-rear direction in each cuvette 15. Therefore accuracy of measurement of foreign matter may vary between the cuvettes 15. However, in the detecting unit main body 42 described with reference to FIG. 8, in forming an optical path between the light irradiating unit 51 and the light receiving unit 52, the positions in the front-rear direction of the light irradiating unit 51 and the light receiving unit 52 are shifted according to the index of refraction of a liquid running through the cuvette 15 forming the optical path such that the positions of the respective focuses of the objective lens 53 and the light receiving lens 57 are positioned at the central portions in the front-rear direction of the cuvettes 15A to 15L.

Figure 8:
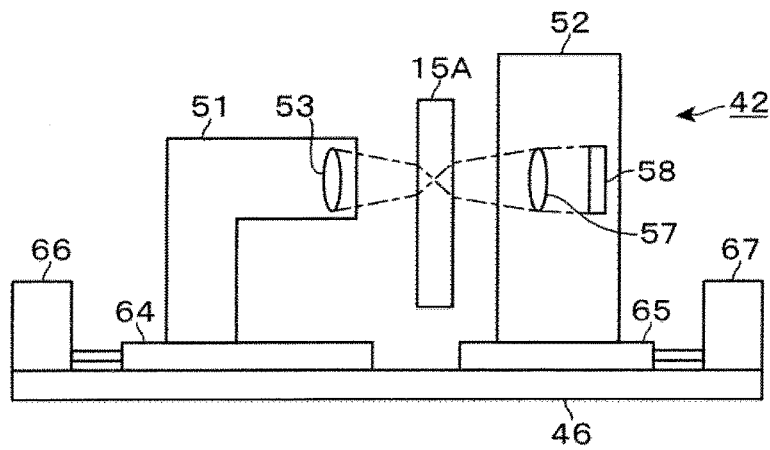
FIG. 8 is a schematic configuration diagram showing another example of constitution of the detecting unit main body.
Figure 9:
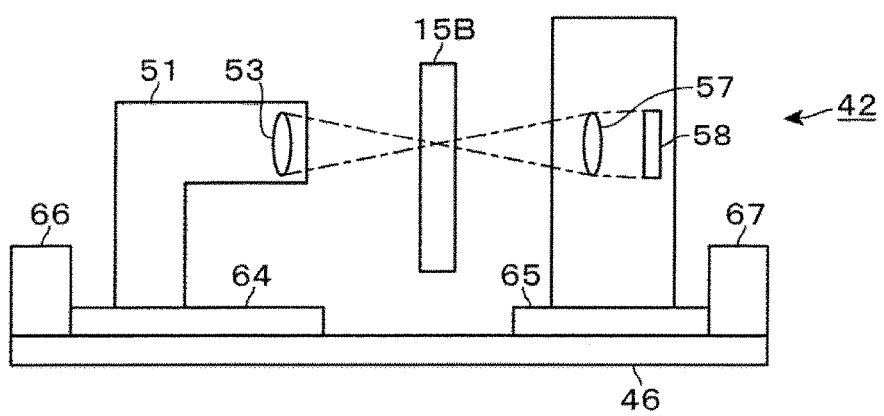
FIG. 9 is a schematic configuration diagram showing the other example of constitution of the detecting unit main body.

As an example, FIG. 8 and FIG. 9 show states in which optical paths are formed in the cuvettes 15A and 15B configured to be supplied with resists having indexes of refraction different from each other. The optical paths are represented by chain lines in the respective figures. The position in the front-rear direction of the light irradiating unit 51 and the position in the front-rear direction of the light receiving unit 52 at a time of formation of the optical path through the cuvette 15A are different from the position in the front-rear direction of the light irradiating unit 51 and the position in the front-rear direction of the light receiving unit 52 at a time of formation of the optical path through the cuvette 15B. The positions of the focuses of the lenses 53 and 57 are thereby made to be the same in the cuvettes 15A and 15B. Because the positions of the focuses are thus made to be the same, variations in accuracy of detection of foreign matter between the cuvettes 15 are suppressed.

Figure 10:
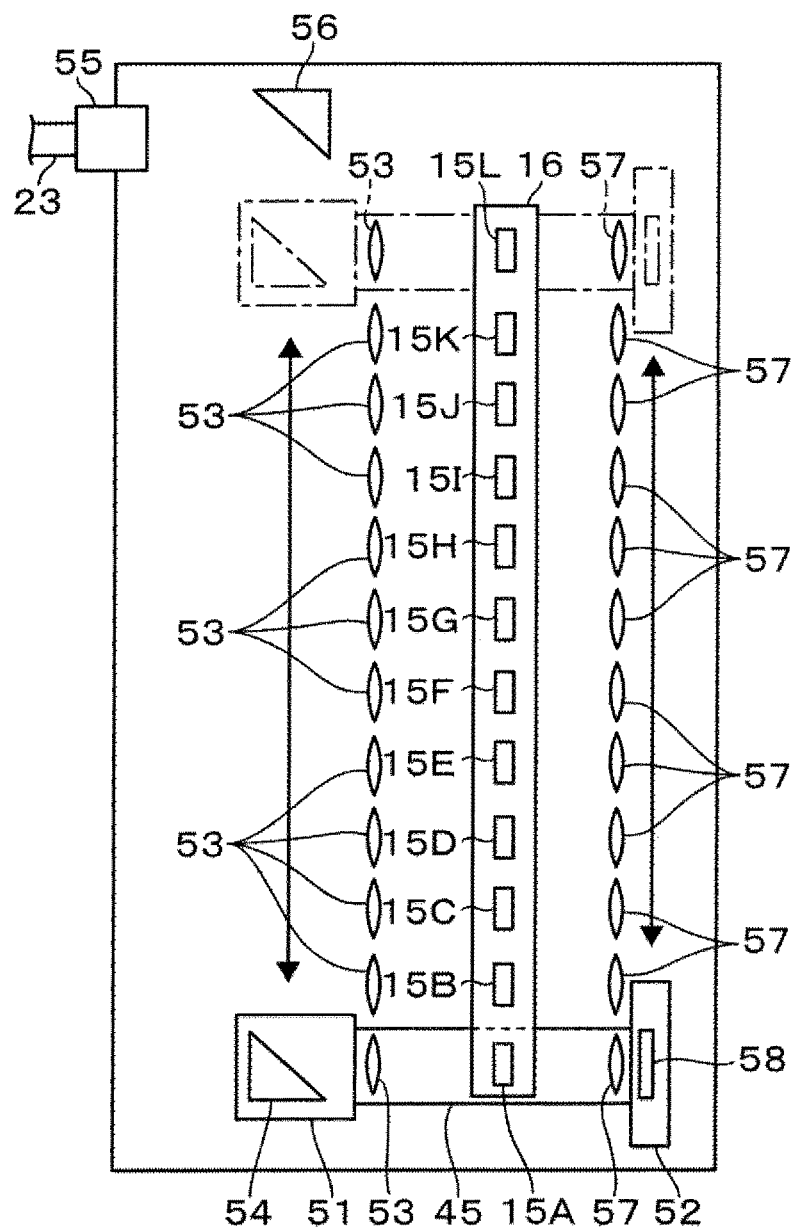
FIG. 10 is a schematic configuration diagram showing yet another example of constitution of the detecting unit main body.

In addition, in the case where the indexes of refraction of the respective liquids running through the cuvettes 15A to 15L are different from each other, instead of forming the detecting unit main body 42 as in FIG. 8 and FIG. 9, as shown in FIG. 10, 12 objective lenses 53 different from each other in focal length may be arranged along the direction of arrangement of the cuvettes 15A to 15L, and 12 light receiving lenses 57 different from each other in focal length may be arranged along the direction of arrangement of the cuvettes 15A to 15L, so that the positions of the focuses of the lenses 53 and 57 in the front-rear direction are made to be the same in each of the cuvettes 15. In the example shown in FIG. 10, unlike the example described with reference to FIG. 4 and the like, only the moving mirror 54 of the objective lens 53 and the moving mirror 54 in the light irradiating unit 51 is moved in the above-described arrangement direction, and the moving mirror 54 guides light to an arbitrary one of the objective lenses 53. In addition, the light receiving unit 52 is configured such that only the light receiving element 58 of the light receiving lens 57 and the light receiving element 58 is moved in the arrangement direction.

Figure 11:
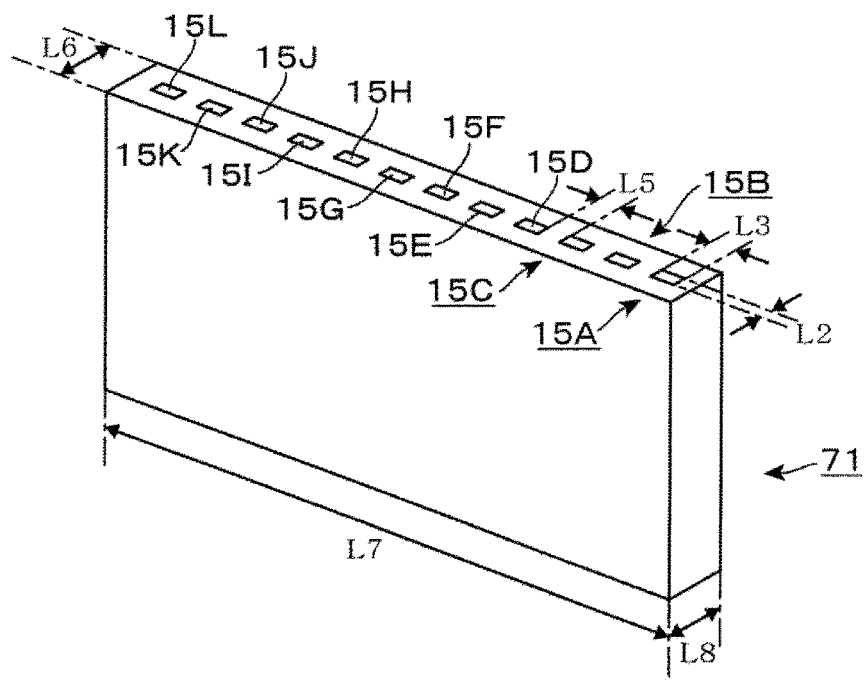
FIG. 11 is a perspective view of another example of constitution of a flow passage array forming the detecting unit main body.
Figure 12:
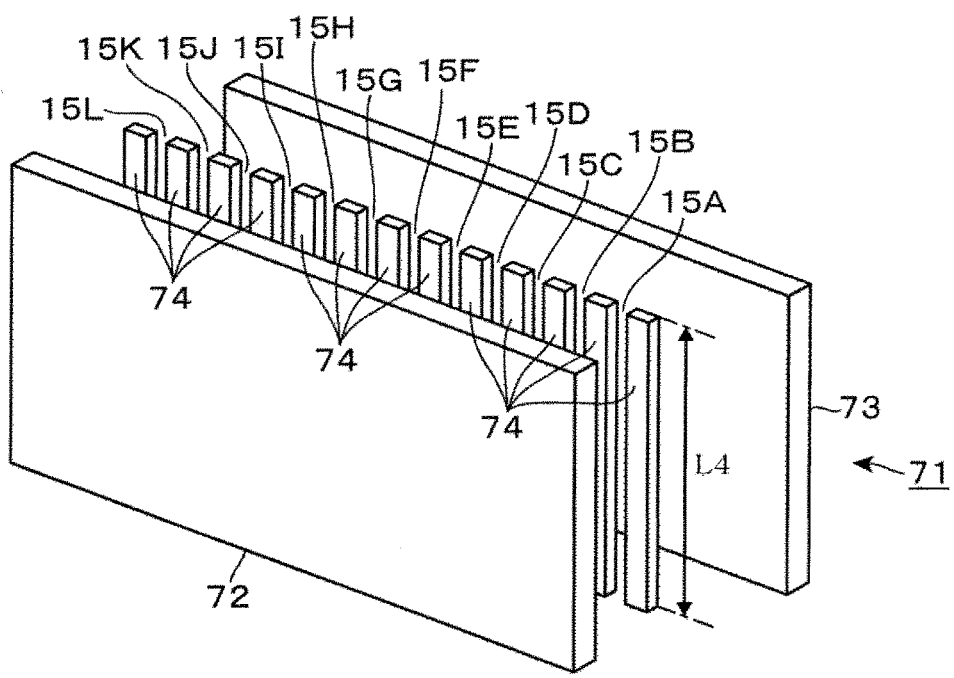
FIG. 12 is an exploded perspective view of the flow passage array.

Another constitution of the flow passage array will be described with reference to FIGS. 11 and 12. FIG. 11 and FIG. 12 are a perspective view and an exploded perspective view of a flow passage array 71. The flow passage array 71 is formed as a rectangular parallelepiped block. The flow passage array 71 includes erected plate-shaped supports 72 and 73 and a plurality of erected angular rod-shaped partition wall forming members 74 disposed so as to be sandwiched between the supports 72 and 73. The partition wall forming members 74 are arranged so as to be orthogonal to a direction of arrangement of the supports 72 and 73. The supports 72 and 73 and the rod-shaped members 74 are formed of quartz, for example.

A plurality of flow passages are formed by joining the supports 72 and 73 and the rod-shaped members 74 to each other, the plurality of flow passages being enclosed by surfaces of the supports 72 and 73 and side surfaces of the partition wall forming members 74, and thus being divided from each other. FIG. 11 and FIG. 12 show these divided flow passages as cuvettes 15A to 15L. Chemicals and test solutions run through these cuvettes 15A to 15L as in the cuvettes 15 of the already described flow passage array 16. The cuvettes 15A to 15L in FIG. 11 and FIG. 12 are formed so as to have a rectangular cross section. Each of the cuvettes 15 has a width L2 of 0.2 mm in a front-rear direction, a width L3 of 2.0 mm in a left-right direction (direction of arrangement of the cuvettes 15), and a height L4 of 25.0 mm, for example. A distance L5 between cuvettes 15 adjacent to each other is for example 3.0 mm.

In addition, the flow passage array 71 has a width L6 of 3.2 mm in the front-rear direction, a width L7 of 63.0 mm in the left-right direction, and a height L8 of 25.0 mm, for example. The flow passage array 71 is for example stored in a case formed of a resin or a metal such as aluminum or the like, and is included in the detecting unit main body 42. An opening portion is provided at a position corresponding to each of the cuvettes 15 in the case so that the already described optical paths can be formed between the light irradiating unit 51 and the light receiving unit 52.

Figure 13:
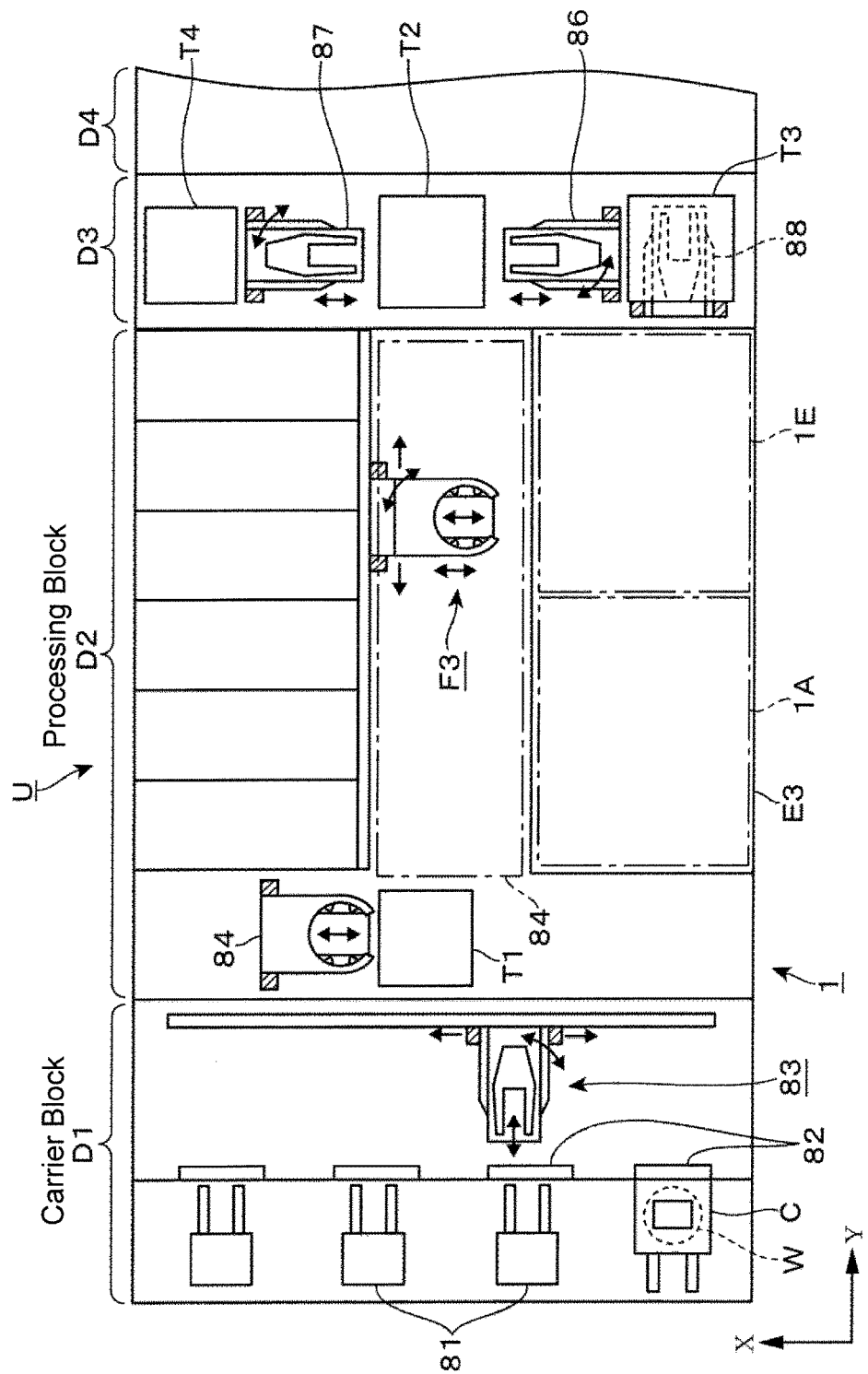
FIG. 13 is a detailed plan view of the coating and developing apparatus.
Figure 14:
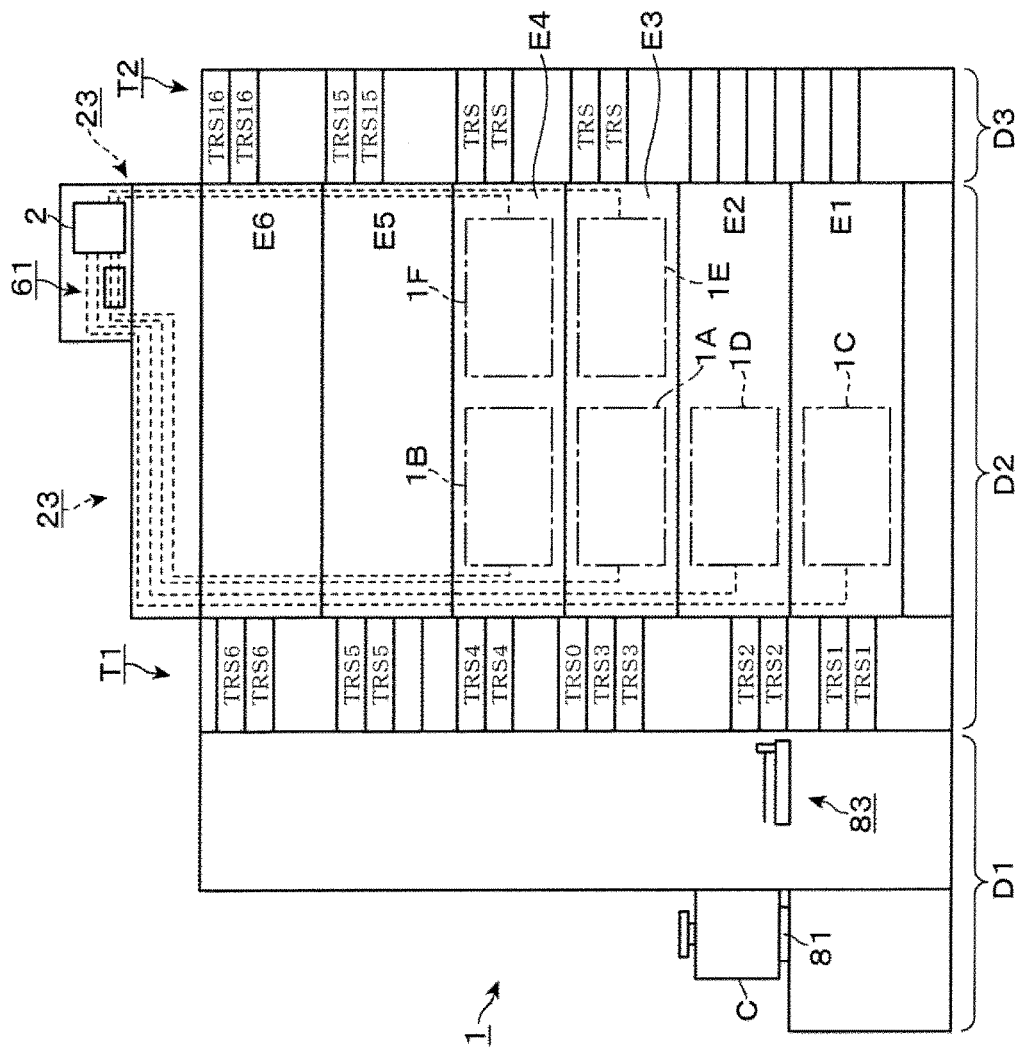
FIG. 14 is a schematic vertical sectional side view of the coating and developing apparatus.

A concrete example of configuration of the coating and developing apparatus 1 will next be described with reference to FIG. 13 and FIG. 14. FIGS. 13 and 14 are a plan view and a schematic vertical sectional side view, respectively, of the coating and developing apparatus 1. The coating and developing apparatus 1 is formed by linearly connecting a carrier block D1, a processing block D2, and an interface block D3. A light exposure device D4 is connected to the interface block D3. The carrier block D1 carries a carrier C into and out of the coating and developing apparatus 1. The carrier block D1 includes a mounting base 81 for the carrier C, an opening and closing portion 82, and a transfer mechanism 83 for transferring a wafer W from the carrier C through the opening and closing portion 82.

The processing block D2 is formed by stacking, in order from the bottom, a first to a sixth unit block E1 to E6 that subject the wafer W to liquid processing. The unit blocks E1 to E6 are divided from each other, and include transfer mechanisms F1 to F6, respectively. The transfer and processing of wafers W are performed in parallel with each other in the unit blocks E.

The third unit block E3 will be described in the following as a representative of the unit blocks with reference to FIG. 13. A transfer region 84 is formed so as to extend from the carrier block D1 to the interface block D3. The above-described transfer mechanism F3 is provided in the transfer region 84. In addition, a shelf unit U is disposed on the left side of the transfer region 84 as viewed in a direction from the carrier block D1 to the interface block D3. The shelf unit U includes a heating module. In addition, the resist coating module 1A and the protective film forming module 1E described above are provided along the transfer region 84 on the right side of the transfer region 84 as viewed in the direction from the carrier block D1 to the interface block D3.

The fourth unit block E4 is configured in a similar manner to the third unit block E3. The fourth unit block E4 is provided with the resist coating module 1B and the protective film forming module 1F. The unit blocks E1 and E2 are configured in a similar manner to the unit blocks E3 and E4 except that the unit blocks E1 and E2 are provided with the antireflection film forming modules 1C and 1D, respectively, in place of the resist coating modules 1A and 1B and the protective film forming modules 1E and 1F. The unit blocks E5 and E6 include a developing module that develops a resist film by supplying a developer to the wafer W. The developing modules are configured in a similar manner to the modules 1A to 1F except that the developing modules supply a developer as a chemical to the wafer W.

Provided on the carrier block D1 side of the processing block D2 are a tower T1 that extends vertically so as to span the unit blocks E1 to E6 and a transfer mechanism 85 for transferring the wafer W to and from the tower T1, the transfer mechanism 85 being capable of being raised and lowered. The tower T1 includes a plurality of modules stacked on each other. The modules provided at respective heights of the unit blocks E1 to E6 can transfer the wafer W to and from the respective transfer mechanisms F1 to F6 of the unit blocks E1 to E6. These modules include a transferring module TRS provided at the height position of each unit block, a temperature control module CPL that adjusts the temperature of the wafer W, a buffer module that temporarily stores a plurality of wafers W, a hydrophobizing processing module that hydrophobizes the surface of the wafer W, and the like. To simplify description, the hydrophobizing processing module, the temperature control module, and the buffer module are not shown in the figures.

The interface block D3 includes towers T2, T3, and T4 that extend vertically so as to span the unit blocks E1 to E6, and is provided with a transfer mechanism 86 for transferring the wafer W to and from the tower T2 and the tower T3, the transfer mechanism 86 being a transferring mechanism capable of being raised and lowered, a transfer mechanism 87 for transferring the wafer W to and from the tower T2 and the tower T4, the transfer mechanism 87 being a transferring mechanism capable of being raised and lowered, and a transfer mechanism 88 for transferring the wafer W to and from the tower T2 and the light exposure device D4.

The tower T2 is formed by stacking transferring modules TRS, a buffer module that stores and retains a plurality of wafers W before light exposure processing, a buffer module that stores the plurality of wafers W after the light exposure processing, a temperature control module that adjusts the temperature of the wafers W, and the like on each other. However, the buffer modules and the temperature control module are not shown in the figures.

The already described light supply unit 2 is provided above the processing block D2. The fibers 23 are routed downward to be connected from the light supply unit 2 to the modules 1A to 1F in the unit blocks E1 to E4. In addition, an arithmetic unit 61 is provided above the processing block D2, the arithmetic unit 61 constituting the above-described control unit 5, and calculating a total number of pieces of foreign matter running through the cuvettes 15 and the particle diameter of each piece of foreign matter on the basis of an output signal from the already described light receiving element 58. The arithmetic unit 61 is connected to the modules 1A to 1F by wiring not shown in the figures. With such a configuration, the already described foreign matter detection is performed in each of the modules 1A to 1F arranged at positions separated from each other.

Paths of transfer of wafers W in the coating and developing apparatus 1 will be described. The transfer mechanism 83 transfers wafers W from the carrier C to the transferring module TRS0 of the tower T1 in the processing block D2. The wafers W from the transferring module TRS0 are allocated and transferred to the unit blocks E1 and E2. For example, when the wafers W are transferred to the unit block E1, the wafers W are transferred from the TRS0 to the transferring module TRS1 corresponding to the unit block E1 (transferring module to and from which the wafers W can be transferred by the transfer mechanism F1) among the transferring modules TRS of the tower T1. When the wafers W are transferred to the unit block E2, the wafers W are transferred from the TRS0 to the transferring module TRS2 corresponding to the unit block E2 among the transferring modules TRS of the tower T1. The transfer of these wafers W is performed by the transfer mechanism 85.

The thus allocated wafers W are transferred from TRS1 (TRS2) to the antireflection film forming module 1C (1D) to the heating module to TRS1 (TRS2) in this order, and are next allocated by the transfer mechanism 85 to the transferring module TRS3 corresponding to the unit block E3 and the transferring module TRS4 corresponding to the unit block E4.

The wafers W thus allocated to TRS3 (TRS4) are transferred from TRS3 (TRS4) to the resist coating module 1A (1B) to the heating module to the protective film forming module 1E (1F) to the heating module to the transferring module TRS of the tower T2 in this order. The transfer mechanisms 86 and 88 thereafter carry the wafers W into the light exposure device D4 via the tower T3. The wafers W after light exposure are transferred between the towers T2 and T4 by the transfer mechanisms 88 and 87, and transferred to the transferring modules TRS15 and TRS16 of the tower T2, the transferring modules TRS15 and TRS16 corresponding to the unit blocks E5 and E6, respectively. The wafers W are thereafter transferred from the heating module to the developing module to the heating module to the transferring module TRS5 (TRS6), and are then returned to the carrier C via the transfer mechanism 83.

The present invention may be applied to the developing modules of the above-described unit blocks E5 and E6 to detect foreign matter in the developers. The present invention is also applicable to chemical supply devices such for example as a device that supplies a chemical for forming an insulating film on a wafer W, a cleaning device that supplies a cleaning solution as a chemical for cleaning a wafer W, a device that supplies an adhesive for laminating a plurality of wafers W to each other as a chemical to the wafers W, and the like. Incidentally, the above-described cleaning device supplies the wafer W with for example pure water, isopropyl alcohol (IPA), or a liquid mixture of ammonia water and hydrofluoric acid which liquid mixture is referred to as SC1. Accordingly, the pure water, IPA, and SC1 may respectively flow through the plurality of cuvettes 15 constituting one flow passage array 16.

In addition, the cuvettes 15 of one flow passage array 16 are not limited to the constitution in which only chemicals used in one module flow through the cuvettes 15. For example, the resists used in the resist coating module 1A and chemicals for forming protective film which chemicals are used in the protective film forming module 1E may be configured to flow through the cuvettes 15 of one flow passage array 16. That is, supposing that the apparatus is provided with a first processing unit and a second processing unit (plurality of processing units) for performing liquid processing by supplying respective chemicals to a wafer W, and that, for example, the first processing unit is provided with a plurality of first flow passages supplying respective chemicals to the wafer W and the second processing unit is provided with a plurality of second flow passages supplying respective chemicals to the wafer W, the detection of foreign matter in the first flow passages and the second flow passages can be performed by the light supply unit 51 and the light receiving unit 52 made common to these first and second flow passages. In this case, the light supply unit 51 and the light receiving unit 52 may be made common to one of the plurality of first flow passages and one of the plurality of second flow passages, the light supply unit 51 and the light receiving unit 52 may be made common to the plurality of first flow passages and the plurality of second flow passages, or the light supply unit 51 and the light receiving unit 52 may be made common to one of the plurality of first flow passages and the plurality of second flow passages. Incidentally, as described above, of the light supply unit 51 and the light receiving unit 52, only the light supply unit 51 may be made common.

In addition, the present invention is not limited to being applied to chemical supply devices. For example, the flow passage array 16 is provided with a cuvette 15 for gas supply which cuvette is different from the cuvettes 15 through which chemicals flow. Then, a suction pump or the like supplies the cuvette 15 for gas supply with an atmosphere in a region to which a wafer W is transferred, such as the transfer region 84 or the like in the coating and developing apparatus 1. The region to which the wafer W is transferred includes a region in which the wafer W is processed, such as the resist coating module 1A or the like. Then, as in the case of detecting foreign matter in a chemical, an optical path is formed through the cuvette for gas supply and foreign matter is detected while a gas flows through the cuvette. That is, the present invention can detect foreign matter included in a fluid supplied to the wafer W.

Foreign matter in a gas in which the wafer W is processed may be detected in addition to the gas forming the atmosphere to which the wafer is transferred as described above. For example, in the above-described developing modules, after a developer is supplied to the wafer W, and pure water for surface cleaning is supplied, a N2 gas for drying the surface of the wafer W is supplied from a nozzle. Detection of foreign matter included in the N2 gas flowing through a supply path to the nozzle may be performed in a similar manner to detection of foreign matter included in the above-described resists. Incidentally, the cuvettes 15 are not limited to being arranged on a straight line, but may be arranged on a curve. Further, the already described examples may be combined with each other.

The invention claimed is:

1. A substrate processing apparatus for processing a substrate by supplying a fluid to the substrate, the substrate processing apparatus comprising:
   measurement flow passage portions as part of a respective plurality of supply paths of fluids to be supplied to the substrate, the measurement flow passage portions constituting measurement regions for measurement of foreign matter in the fluids, and being disposed so as to form a row with each other;
   a light irradiating unit configured to form an optical path in one of the flow passage portions, the light irradiating unit being shared by the plurality of flow passage portions;
   a moving mechanism configured to move the light irradiating unit relatively along a direction of arrangement of the flow passage portions to form the optical path within the flow passage portion selected among the plurality of flow passage portions;
   a light receiving unit including a light receiving element, the light receiving element receiving light transmitted by the flow passage portion; and
   a detecting unit configured to detect foreign matter in the fluid on a basis of a signal output from the light receiving element, wherein
   fluids having indexes of refraction different from each other flow through one flow passage portion and another flow passage portion among the plurality of flow passage portions, and
   a lens displacing mechanism is provided, the lens displacing mechanism displacing a condensing lens included in a light irradiating optical system and a light receiving lens included in a light receiving optical system in a direction of the optical path according to the indexes of refraction of the fluids.

2. The substrate processing apparatus according to claim 1, wherein
   the light irradiating unit and the light receiving unit include the light irradiating optical system and the light receiving optical system, respectively,
   the light irradiating optical system and the light receiving optical system are shared by the plurality of flow passage portions, and
   the moving mechanism is configured to move the light irradiating optical system and the light receiving optical system relatively along the direction of arrangement of the flow passage portions.

3. The substrate processing apparatus according to claim 1, wherein
   a test flow passage portion as a part of a flow passage of a test fluid including test particles at a preset ratio, the test flow passage portion constituting a measurement region for measurement of the test particles in the test fluid, is provided at a position along the direction of arrangement of the measurement flow passage portions,
   the light irradiating unit selects one of the measurement flow passage portions and the test flow passage portion, and forms the optical path, and
   the detecting unit detects the foreign matter in the fluid in the measurement flow passage portion on the basis of a signal output from the light receiving element when the light irradiating unit forms the optical path in the test flow passage portion.

4. A substrate processing apparatus for processing a substrate by supplying a fluid to the substrate, the substrate processing apparatus comprising:
- measurement flow passage portions as part of a respective plurality of supply paths of fluids to be supplied to the substrate, the measurement flow passage portions constituting measurement regions for measurement of foreign matter in the fluids, and being disposed so as to form a row with each other;
- a light irradiating unit configured to form an optical path in one of the flow passage portions, the light irradiating unit being shared by the plurality of flow passage portions;
- a moving mechanism configured to move the light irradiating unit relatively along a direction of arrangement of the flow passage portions to form the optical path within the flow passage portion selected among the plurality of flow passage portions;
- a light receiving unit including a light receiving element, the light receiving element receiving light transmitted by the flow passage portion; and
- a detecting unit configured to detect foreign matter in the fluid on a basis of a signal output from the light receiving element, wherein
- fluids having indexes of refraction different from each other flow through one flow passage portion and another flow passage portion among the plurality of flow passage portions,
- the light irradiating unit includes a plurality of condensing lenses having focal lengths different from each other according to the indexes of refraction of the fluids, and
- the light receiving unit includes a plurality of light receiving lenses having focal lengths different from each other according to the indexes of refraction of the fluids.

5. The substrate processing apparatus according to claim 4, wherein
- the light irradiating unit and the light receiving unit include a light irradiating optical system and a light receiving optical system, respectively,
- the light irradiating optical system and the light receiving optical system are shared by the plurality of flow passage portions, and
- the moving mechanism is configured to move the light irradiating optical system and the light receiving optical system relatively along the direction of arrangement of the flow passage portions.

6. The substrate processing apparatus according to claim 4, wherein
- a test flow passage portion as a part of a flow passage of a test fluid including test particles at a preset ratio, the test flow passage portion constituting a measurement region for measurement of the test particles in the test fluid, is provided at a position along the direction of arrangement of the measurement flow passage portions,
- the light irradiating unit selects one of the measurement flow passage portions and the test flow passage portion, and forms the optical path, and
- the detecting unit detects the foreign matter in the fluid in the measurement flow passage portion on the basis of a signal output from the light receiving element when the light irradiating unit forms the optical path in the test flow passage portion.

7. A substrate processing apparatus for processing a substrate by supplying a fluid to the substrate, the substrate processing apparatus comprising:
- measurement flow passage portions as part of a respective plurality of supply paths of fluids to be supplied to the substrate, the measurement flow passage portions constituting measurement regions for measurement of foreign matter in the fluids, and being disposed so as to form a row with each other;
- a light irradiating unit configured to form an optical path in one of the flow passage portions, the light irradiating unit being shared by the plurality of flow passage portions;
- a moving mechanism configured to move the light irradiating unit relatively along a direction of arrangement of the flow passage portions to form the optical path within the flow passage portion selected among the plurality of flow passage portions;
- a light receiving unit including a light receiving element, the light receiving element receiving light transmitted by the flow passage portion;
- a detecting unit configured to detect foreign matter in the fluid on a basis of a signal output from the light receiving element;
- a plurality of groups each including the plurality of flow passage portions, the light irradiating unit, the moving mechanism, and the light receiving unit;
- a light source common to the groups; and
- a split light path forming unit configured to form an optical path branching on a downstream side to split light of the light source for each group.

8. The substrate processing apparatus according to claim 7, wherein
- the light irradiating unit and the light receiving unit include a light irradiating optical system and a light receiving optical system, respectively,
- the light irradiating optical system and the light receiving optical system are shared by the plurality of flow passage portions, and
- the moving mechanism is configured to move the light irradiating optical system and the light receiving optical system relatively along the direction of arrangement of the flow passage portions.

9. The substrate processing apparatus according to claim 7, wherein
- a test flow passage portion as a part of a flow passage of a test fluid including test particles at a preset ratio, the test flow passage portion constituting a measurement region for measurement of the test particles in the test fluid, is provided at a position along the direction of arrangement of the measurement flow passage portions,
- the light irradiating unit selects one of the measurement flow passage portions and the test flow passage portion, and forms the optical path, and
- the detecting unit detects the foreign matter in the fluid in the measurement flow passage portion on the basis of a signal output from the light receiving element when the light irradiating unit forms the optical path in the test flow passage portion.

10. A substrate processing method for processing a substrate by supplying a fluid to the substrate, the substrate processing method comprising:
- a step of forming an optical path in measurement flow passage portions by using a light irradiating unit shared by measurement flow passage portions, the measurement flow passage portions being part of a respective plurality of supply paths of fluids to be supplied to the substrate, and the measurement flow passage portions constituting measurement regions for measurement of foreign matter in the fluids and being disposed so as to form a row with each other;

a step of moving the light irradiating unit relatively along a direction of arrangement of the flow passage portions by a moving mechanism to form the optical path within the flow passage portion selected among the plurality of flow passage portions;

a step of receiving light transmitted by the flow passage portion by a light receiving element included in a light receiving unit; and a step of detecting foreign matter in the fluid by a detecting unit on a basis of a signal output from the light receiving element, wherein the light irradiating unit and the light receiving unit include a light irradiating optical system and a light receiving optical system, respectively, the light irradiating optical system and the light receiving optical system are shared by the plurality of flow passage portions, and the substrate processing method includes a step of moving, by the moving mechanism, the light irradiating optical system and the light receiving optical system relatively along the direction of arrangement of the flow passage portions.

11. The substrate processing method according to claim 10, further comprising:

a step of making fluids having indexes of refraction different from each other flow through one flow passage portion and another flow passage portion, respectively, among the plurality of flow passage portions; and a step of displacing, by a lens displacing mechanism, a condensing lens included in the light irradiating optical system and a light receiving lens included in the light receiving optical system in a direction of the optical path according to the indexes of refraction of the fluids.

12. The substrate processing method according to claim 10, wherein a test flow passage portion as a part of a flow passage of a test fluid including test particles at a preset ratio, the test flow passage portion constituting a measurement region for measurement of the test particles in the test fluid, is provided at a position along the direction of arrangement of the measurement flow passage portions, the substrate processing method includes a step of selecting either the measurement flow passage portions or the test flow passage portion and forming the optical path by the light irradiating unit, and the step of detecting the foreign matter in the fluid in the measurement flow passage portion by the detecting unit includes a step of detecting the foreign matter in the fluid in the measurement flow passage portion on the basis of a signal output from the light receiving element when the optical path is formed in the test flow passage portion.

* * * * *